United States Patent
O'Keefe et al.

(10) Patent No.: US 9,982,025 B2
(45) Date of Patent: May 29, 2018

(54) MONOMERIC GRIFFITHSIN TANDEMERS

(71) Applicant: The United States of America, as represented by the Secretary, Department of Health and Human Services, Washington, DC (US)

(72) Inventors: Barry R. O'Keefe, Frederick, MD (US); Alexander Wlodawer, Frederick, MD (US); Tinoush Moulaei, College Park, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days. days.

(21) Appl. No.: 14/895,349

(22) PCT Filed: Jun. 5, 2014

(86) PCT No.: PCT/US2014/040992
§ 371 (c)(1),
(2) Date: Dec. 2, 2015

(87) PCT Pub. No.: WO2014/197650
PCT Pub. Date: Dec. 11, 2014

(65) Prior Publication Data
US 2016/0108097 A1    Apr. 21, 2016

Related U.S. Application Data

(60) Provisional application No. 61/831,336, filed on Jun. 5, 2013.

(51) Int. Cl.
C07K 14/405 (2006.01)
A61K 47/48 (2006.01)
A61K 38/00 (2006.01)

(52) U.S. Cl.
CPC .......... *C07K 14/405* (2013.01); *A61K 47/481* (2013.01); *A61K 47/4823* (2013.01);
(Continued)

(58) Field of Classification Search
None
See application file for complete search history.

(56) References Cited

U.S. PATENT DOCUMENTS 7,884,178 B2    2/2011    Boyd et al.
8,088,729 B2    1/2012    O'Keefe et al.
(Continued)

FOREIGN PATENT DOCUMENTS

EP    2314349 A1  * 12/2006    .............. A61P 31/12
EP    1740605 A2    1/2007

OTHER PUBLICATIONS

Mori et al. "Isolation and Characterization of Griffithsin, a Novel HIV-inactivating Protein, from the Red Alga *Griffithsia* sp." J. Biol. Chem. 2005; 280(10): 9345-9353.*
(Continued)

*Primary Examiner* — Janet L Andres
*Assistant Examiner* — Stuart W Snyder
(74) *Attorney, Agent, or Firm* — Leydig, Voit & Mayer, Ltd.

(57) ABSTRACT

The invention provides a construct containing two or more monomeric griffithsin molecules, optionally joined by a linker, as well as conjugate comprising the construct, a nucleic acid encoding the construct or conjugate, vectors, and cells. A nucleic acid encoding the polypeptide or fusion protein, as well as compositions or cells comprising the polypeptide, fusion protein, or nucleic acid also are provided.

18 Claims, 2 Drawing Sheets

Figure 1:
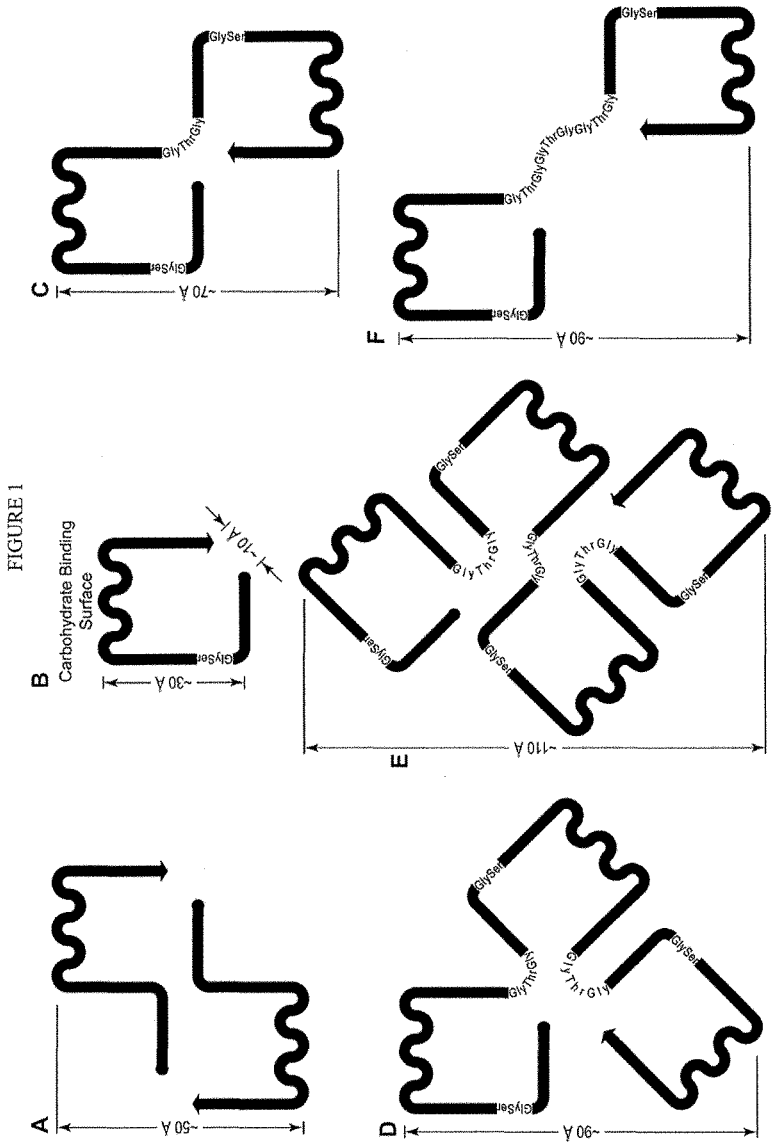

(52) U.S. Cl.
CPC .. *A61K 47/48215* (2013.01); *A61K 47/48246* (2013.01); *A61K 47/48284* (2013.01); *A61K 47/48338* (2013.01); *A61K 38/00* (2013.01); *C07K 2319/00* (2013.01)

(56) References Cited

U.S. PATENT DOCUMENTS

2009/0297516 A1 12/2009 Mayo et al.
2011/0263485 A1 10/2011 Liwang et al.

OTHER PUBLICATIONS

Robinson and Sauer Optimizing the stability of single-chain proteins by linker length and composition mutagenesis. Proc. Natl. Acad. Sci. USA, 1998; 95: 5929-5934.*
Alexandre et al., "Mannose-rich glycosylation patterns on HIV-1 subtype C gp120 and sensitivity to the lectins, Griffithsin, Cyanovirin-N and Scytovirin," *Virology*, 402(1): 187-196 (2010).
Balzarini et al., "Carbohydrate-binding agents: a potential future cornerstone for the chemotherapy of enveloped viruses?," *Antivir. Chem. Chemother.*, 18(1): 1-11 (2007).
Banerjee et al., "Occluding the Mannose Moieties on Human Immunodeficiency Virus Type 1 gp120 with Griffithsin Improves the Antibody Responses to Both Proteins in Mice," *AIDS Research and Human Retroviruses*, 28(2): 206-214 (2012).
Bourne et al., "Structural basis for the unusual carbohydrate-binding specificity of jacalin towards galactose and mannose," *Biochem. J.*, 364(Pt. 1): 173-180 (2002).
GENPEPT Accession No. 3LL2_A (Oct. 10, 2012).
Huang et al., "Removal of two high-mannose N-linked glycans on gp120 renders human immunodeficiency virus 1 largely resistant to the carbohydrate-binding agent griffithsin," *J. Gen. Virol.*, 92(10): 2367-2373 (2011).
Jeyaprakash et al., "Structural Basis of the Carbohydrate Specificities of Jacalin: An X-ray and Modeling Study," *J. Mol. Biol.*, 332(1): 217-228 (2003).
Keeffe et al., "Designed oligomers of cyanovirin-N show enhanced HIV neutralization," *Proceedings of National Academy of Sciences USA*, 108(34): 14079-14084 (2011).
Klein et al., "Few and Far Between: How HIV May Be Evading Antibody Avidity," *PLoS Pathog.*, 6(5): e1000908 (2010).
Kouokam et al., "Investigation of Griffithsin's Interactions with Human Cells Confirms Its Outstanding Safety and Efficacy Profile as a Microbicide Candidate," *PLoS One*, 6(8): e22635 (2011).
Kwong et al., "HIV-1 evades antibody-mediated neutralization through conformational masking of receptor-binding sites," *Nature*, 420(6916): 637-682 (2002).
Labrijn et al., "Access of Antibody Molecules to the Conserved Coreceptor Binding Site on Glycoprotein gp120 Is Sterically Restricted on Primary Human Immunodeficiency Virus Type 1," *J. Virol.*, 77(19): 10557-10565 (2003).
Leonard et al., "Assignment of Intrachain Disulfide Bonds and Characterization of Potential Glycosylation Sites of the Type 1 Recombinant Human Immunodeficiency Virus Envelope Glycoprotein (gp120) Expressed in Chinese Hamster Ovary Cells," *J. Biol. Chem.*, 265(18): 10373-10382 (1990).
Meuleman et al., "Griffithsin Has Antiviral Activity against Hepatitis C Virus," *Antimicrob. Agents Chemother.*, 55(11): 5159-5167 (2011).
Mori et al., "Isolation and Characterization of Griffithsin, a Novel HIV-inactivating Protein, from the Red Alga *Griffithsia* sp.," *J. Biol. Chem.*, 280(10): 9345-9353 (2005).
Moulaei et al., "Monomerization of the viral entry inhibitor griffithsin yields insights into the relationship between multivalent binding to high mannose oligosaccharides and antiviral activity," *Structure*, 18(9): 1104-1115 (2010).
O'Keefe et al., "Broad-Spectrum In Vitro Activity and In Vivo Efficacy of the Antiviral Protein Griffithsin against Emerging Viruses of the Family Coronaviridae," *J. Virol.*, 84(5): 2511-2521 (2010).
O'Keefe et al., "Scaleable manufacture of HIV-1 entry inhibitor griffithsin and validation of its safety and efficacy as a topical microbicide component," *Proc. Natl. Acad. Sci. USA*, 106(15): 6099-6104 (2009).
Rabesseda, "A Report From the 26th International Conference on Antiviral Research (May 11-15, San Francisco, California, USA)," *Drugs of Today*, 49(6): 411-417 (2013).
Starcich et al., "Identification and Characterization of Conserved and Variable Regions in the Envelope Gene of HTLV-III/LAV, the Retrovirus of AIDS," *Cell*, 45(5): 637-648 (1986).
Toone et al., "Structure and energetic of protein-carbohydrate complexes," *Current Opinion in Structural Biology*, 4(5): 719-728 (1994).
Wei et al., "Antibody neutralization and escape by HIV-1," *Nature*, 422(6929): 307-312 (2003).
Wyatt et al., "The HIV-1 Envelope Glycoproteins: Fusogens, Antigens, and Immunogens," *Science*, 280(5371): 1884-1888 (1998).
Xue et al., "The Griffithsin Dimer Is Required for High-Potency Inhibition of HIV-1: Evidence for Manipulation of the Structure of gp120 as Part of the Griffithsin Dimer Mechanism," *Antimicrobial Agents and Chemotherapy*, 57(8): 3976-3989 (2013).
Zeitlin et al., "Second-generation HIV microbicides: Continued development of griffithsin," *Proc. Natl. Acad. Sci. USA*, 106(15): 6029-6030 (2009).
Ziolkowska et al., "Structural studies of algal lectins with anti-HIV activity," *Acta Biochim. Pol.*, 53(4): 617-626 (2006).
Ziolkowska et al., "Crystallographic studies of the complexes of antiviral protein griffithsin with glucose and N-acetylglucosamine," *Protein Sci.*, 16(7): 1485-1489 (2007).
Ziolkowska et al., "Domain-Swapped Structure of the Potent Antiviral Protein Griffithsin and Its Mode of Carbohydrate Binding," *Structure*, 14(7): 1127-1135 (2006).

* cited by examiner

FIGURE 2

MONOMERIC GRIFFITHSIN TANDEMERS

CROSS-REFERENCE TO RELATED APPLICATIONS

This patent application is the U.S. National Phase of Patent Application No. PCT/US2014/040992, filed Jun. 5, 2014, which claims the benefit of U.S. Provisional Patent Application No. 61/831,336, filed Jun. 5, 2013, which is incorporated by reference.

STATEMENT REGARDING FEDERALLY SPONSORED RESEARCH OR DEVELOPMENT

This invention was made with Government support under project numbers 1ZIABC011472 and 1ZIABC011469 by the National Institutes of Health, National Cancer Institute. The Government has certain rights in the invention.

INCORPORATION-BY-REFERENCE OF MATERIAL SUBMITTED ELECTRONICALLY SEQUENCE LISTING

Incorporated by reference in its entirety herein is a nucleotide/amino acid sequence listing submitted concurrently herewith and identified as follows: One 21,649 Byte ASCII (Text) file named "722350_ST25.TXT," created on Dec. 2, 2015.

SEQUENCE LISTING

Incorporated by reference in its entirety herein is a nucleotide/amino acid sequence listing submitted concurrently herewith.

BACKGROUND OF THE INVENTION

The surface glycoproteins of enveloped viruses act as anchors for docking and fusion with the target host membrane and initiation of another round of viral replication (Wyatt et al., Science, 280(5371): 1884-8 (1998)). These glycoproteins are the most prominent viral surface features that can be recognized within the host cellular background and targeted for antibody neutralization. Consequently, viruses have evolved a number of strategies for shielding the spike structures formed by their glycoproteins. These strategies include restriction of access to conserved structural features through conformational occlusion and oligomerization (Kwong et al., Nature, 420(6916): 678-82 (2002); and Labrijn et al., J. Virol., 77(19): 10557-65 (2003)), sequence hyper-variability especially within loops that mask conserved epitopes (Starcich et al., Cell, 45(5): 637-48 (1986)), and extensive posttranslational glycosylation (Wei et al., Nature, 422(6929): 307-312 (2003)). In case of HIV, the viral defenses appear to be further buttressed by limiting the number of gp120 trimeric spikes present on the HIV envelope and effectively reducing the quantity of viral antigen presented to the immune system (Klein et al., PLoS Pathog., 6(5): e1000908 (2010)).

N-linked carbohydrates compose approximately 50% of the molecular weight HIV gp120 (Leonard et al., J. Biol. Chem., 265(18): 10373-82 (1990)), creating a glycan armor that hides the underlying protein structures. The success of this defensive mechanism may in part hinge on the weak interactions between proteins and carbohydrates (Toone, Current Opinion in Structural Biology, 4(5): 719-728 (1994)). The viral glycan modifications are essential for proper folding and trafficking of viral glycoproteins within the endoplasmic reticulum and trans-Golgi network. Therefore, potential mutations that would reduce the glycosylation levels of HIV glycoproteins could affect processing and maturation of these glycoproteins, leading to attenuated infectivity, as well as exposing the virus to the immune system.

Lectins are small proteins that have evolved to bind carbohydrates with high affinity and specificity. A number of lectins have been shown to display potent antiviral activity (Balzarini et al., Antivir. Chem. Chemother., 18(1): 1-11 (2007)). A potent anti-HIV lectin is griffithsin (GRFT), an obligate domain-swapped dimer in which each domain has jacalin-like fold (Bourne et al., Biochem. J., 364(Pt. 1): 173-80 (2002)). Unlike jacalin in which only a single carbohydrate-binding site is present in each molecule (Jeyaprakash et al., J. Mol. Biol., 332(1): 217-28 (2003)), each domain of GRFT contains three carbohydrate-binding sites, the centers of which form an equilateral 15-A triangle (Ziolkowska et al., Structure, 14(7): 1127-35 (2006)). GRFT has anti-HIV $EC_{50}$ of ~50 pM in cell-based assays (Mori et al., J. Biol. Chem., 280(10): 9345-53 (2005)). GRFT is also active against the coronavirus responsible for SARS (O'Keefe et al., J. Virol., 84(5): 2511-21 (2010); and Zeitlin et al., Proc. Natl. Acad. Sci. USA, 106(15): 6029-30 (2009)) and against the hepatitis C virus (Meuleman et al., Antimicrob. Agents Chemother., 55(11): 5159-67 (2011)).

GRFT is thermostable, can survive in a wide range of conditions including macaque vaginal environment, and exhibits little or no toxicity and immunogenicity (Kouokam et al., PLoS One, 6(8): e22635 (2011)). Large-scale production of GRFT in genetically modified tobacco plants has been demonstrated (O'Keefe et al., Proc. Natl. Acad. Sci. USA, 106(15): 6099-104 (2009)).

The structures of unliganded, native GRFT and its complexes with a number of mono- and disaccharides have been previously identified (Ziolkowska et al., Structure, 14(7): 1127-35 (2006); Ziolkowska et al., Acta Biochim. Pol., 53(4): 617-26 (2006); and Ziolkowska et al., Protein Sci., 16(7): 1485-9 (2007)). Additionally, several monomeric forms of GRFT (mGRFT) have been engineered and their structures solved, including a complex with nonamannoside, an analogue of Man9 and a common glycosylation pattern found on HIV surface glycoproteins. Although, the anti-HIV activity of mGRFT was approximately 1000-fold lower than that of GRFT, both the monomeric and dimeric forms of this lectin have very similar carbohydrate binding affinities.

The need remains for additional griffithsin forms with improved potency.

BRIEF SUMMARY OF THE INVENTION

The invention provides a construct containing two or more monomeric griffithsin molecules, optionally joined by a linker, as well as a conjugate comprising the construct. Nucleic acid molecules encoding the constructs and conjugates, vectors comprising the nucleic acid molecules, cells comprising the nucleic acid molecules or cells, as well as compositions comprising the constructs, conjugates, nucleic acid molecules, vectors, and cells also are provided.

The invention also provides a method of inhibiting a viral (e.g., HIV) infection in a cell, host, biological sample, or inanimate object comprising administering the constructs, conjugates, nucleic acid molecules, vectors, cells, or compositions, such that the viral infection is inhibited.

BRIEF DESCRIPTION OF THE SEVERAL VIEWS OF THE DRAWING(S)

FIGS. 1A-F are schematic representations of griffithsin (GRFT)-based lectins. Native GRFT (A), mGRFT (B), 2mGRFT (2mG) (C), 3mGRFT (3mG) (D), 4mGRFT (4 mg) (E), and 2mGRFT$^{long}$ (2mG3) (F) are represented in an abstract form. Indentations in the tracing represent carbohydrate-binding sites. Gly-Ser insertions prevent domain swapping and result in a monomeric lectin. Gly-Thr-Gly linkers connect the mGRFT domains in tandem repeats. The N- and C-termini in a single mGRFT domain are approximately 10 Å apart, causing the individual domains in the tandemers to branch out. Each GlyThrGly linker is also approximately 10 Å long in its extended conformation. The maximum theoretical dimensions of each lectin were calculated based on their model structures.

Figure 2:
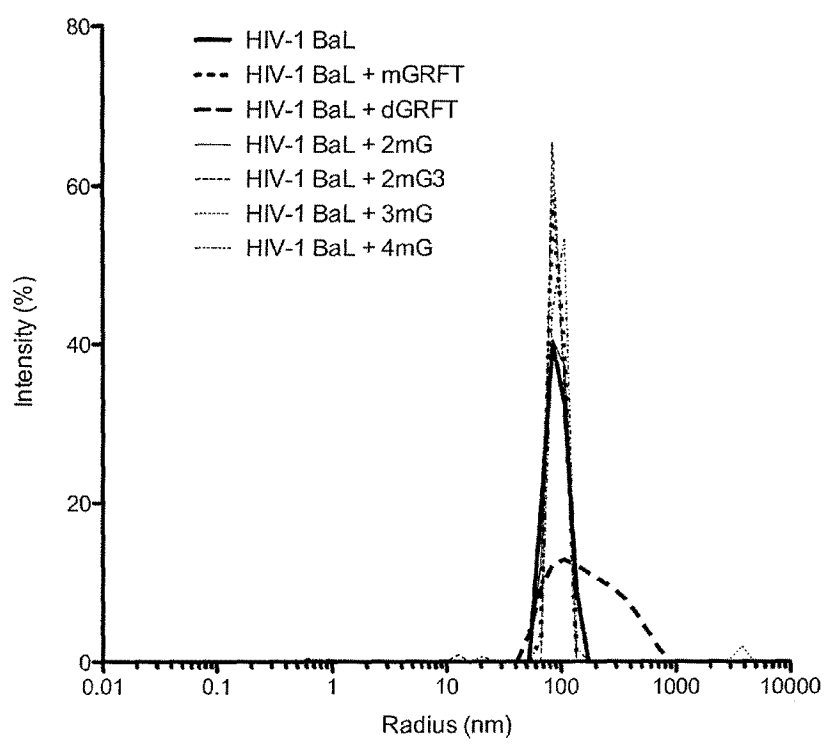

FIG. 2 is a graph illustrating the results of dynamic light scattering experiments on HIB-1$_{BAL}$ virions treated with GRFT, mGRFT or the mGRFT tandemers. Dynamic light scattering traces for HIV-1$_{BAL}$ viruses without lectin, with mGRFT, with dGRFT, or with one of the tandemers. Negative controls with buffers or purified lectin did not measurably scatter light.

DETAILED DESCRIPTION OF THE INVENTION

The invention provides new lectins constructed from tandem repeats of monomeric griffithsin (mGRFT), which have potent antiviral activity. In particular, the invention provides a construct comprising, consisting essentially of, or consisting of two or more mGRFT molecules (domains), optionally joined by a linker.

Any mGRFT can be used in the inventive construct. The mGRFT preferably has an insertion of two or more residues between Ser16 and Gly17 relative to the amino acid sequence of griffithsin (SEQ ID NO: 7). While any residues can be inserted, preferably at least one of the residues is a serine. In one embodiment, the inserted residues are (Gly-Ser)$_n$, wherein n is 1 or 2.

Alternatively or additionally, the mGRFT can contain additional insertions, deletions, substitutions, or additions as long as the GRFT is monomeric. For example, the mGRFT can comprise a substitution at Leu2 relative to the amino acid sequence of griffithsin (SEQ ID NO: 7). In one embodiment, the substitution is Leu2Ser.

The mGRFT additionally or alternatively can include one or more mutations selected from the group consisting of M61V, E75Q, M78K, S106R, A107S, I116F, and E119Q. Although no wishing to be bound by any particular theory, the L2S and (Gly-Ser)$_n$ mutations are related to monomeric structure, the E75Q, M78K, and E119Q mutations are related to pH, the M61V, M78K, and I116F mutations are related to Met oxidation, and the S106R and A107S mutations are related to solubility of mGRFT.

Particular mGRFTs for use in the invention include the mGRFTs described in Moulaei et al., *Structure*, 18(9): 1104-15 (2010), such as IGS-S (Protein Data Bank (PDB) ID 3LL2) and IGS-SDNΔY. Preferably, the inventive mGRFT construct comprises IGS-S.

IGS-S corresponds to the amino acid sequence of SEQ ID NO: 6. IGS-S contains an insertion of a glycine and serine between Ser16 and Gly17 relative to the amino acid sequence of griffithsin (SEQ ID NO: 7). Additionally, IGS-S contains a L2S mutation at the N-terminus. When IGS-S contains an N-terminal activity tag, the L2S mutations renders the monomer more susceptible to proteolytic cleavage of the N-terminal activity tag.

The tandemer construct contains two or more mGRFT molecules (e.g., IGS-S), optionally joined by a linker. Any number of mGRFT molecules can be included in the tandemers, such as two, three, four, five, six, seven, eight, nine, or ten mGRFT molecules. Preferably, two, three, or four mGRFT molecules are included in the tandemer construct.

The mGRFT molecules can be joined via a linker, such as a flexible peptide chain. The linker can be any suitable linker of any length, but is preferably at least about 3 (e.g., 3, 4, 5, 6, 7, 8, 9, 10, 11, or 12) amino acids in length. Examples of suitable linkers include, but are not limited to, linkers that comprise one or more (e.g., two, three, four, five, six, seven, eight, nine, or ten) (Gly-Thr-Gly)$_n$ motifs (wherein n is 1-5), such as the linkers of Gly-Thr-Gly and SEQ ID NOs: 4 and 5.

Particular examples of the inventive mGRFT tandemer constructs include those depicted in FIGS. 1C-F. In each of FIGS. 1C-F, the mGRFT is IGS-S(PDB ID 3LL2). The insertion of the (Gly-Ser)$_n$ (n=1) between Ser16 and Gly17 is noted. In FIGS. 1C-E, the mGRFT molecules are linked using (Gly-Thr-Gly)$_n$ (n=1) linkers. In FIG. 1F, the mGRFT molecules are linked using a (Gly-Thr-Gly)$_n$ (n=3) linker. The tandemers in FIGS. 1C-F correspond to 2mGRFT (2mG), 3mGRFT (3mG), 4mGRFT (4mG), and 2mGRFT-$^{long}$ (2mG3), respectively. Exemplary nucleic acid and amino acid sequences of these GRFT tandemers are shown in Table 2.

If desired, the mGRFT tandemer constructs of the invention can be modified, for instance, by glycosylation, amidation, carboxylation, or phosphorylation, or by the creation of acid addition salts, amides, esters, in particular C-terminal esters, and N-acyl derivatives thereof. The polypeptides also can be modified to create protein derivatives by forming covalent or noncovalent complexes with other moieties in accordance with methods known in the art. Covalently-bound complexes can be prepared by linking the chemical moieties to functional groups on the side chains of amino acids comprising the proteins, or at the N- or C-terminus. Desirably, such modifications and conjugations do not adversely affect the activity of the mGRFT tandemer constructs. While such modifications and conjugations can have greater or lesser activity, the activity desirably is not negated and is characteristic of the unaltered polypeptide.

The mGRFT tandemer constructs can be prepared by any of a number of conventional techniques. For instance, a nucleic acid (e.g., DNA) fragment encoding one or more mGRFT molecules can be subcloned into an appropriate vector using well-known molecular genetic techniques (see, e.g., Maniatis et al., *Molecular Cloning: A Laboratory Manual,* 2nd ed. (Cold Spring Harbor Laboratory (1989)). The fragment can be transcribed and the polypeptide subsequently translated in vitro. Commercially available kits also can be employed (e.g., such as manufactured by Clontech, Palo Alto, Calif.; Amersham Life Sciences, Inc., Arlington Heights, Ill.; Invitrogen, San Diego, Calif.; and the like). The polymerase chain reaction optionally can be employed in the manipulation of nucleic acids.

The mGRFT tandemer constructs also can be synthesized using an automated peptide synthesizer in accordance with methods known in the art. Alternately, mGRFT tandemer constructs can be synthesized using standard peptide synthesizing techniques well-known to those of skill in the art (e.g., as summarized in Bodanszky, *Principles of Peptide Synthesis,* (Springer-Verlag, Heidelberg: 1984)). In particular, the mGRFT tandemer constructs can be synthesized using the procedure of solid-phase synthesis (see, e.g., Merrifield, *J. Am. Chem. Soc.*, 85: 2149-54 (1963); Barany et al., *Int. J. Peptide Protein Res.*, 30: 705-739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The protein-containing mixture then can be extracted, for instance, with diethyl ether, to remove non-peptidic organic compounds, and the synthesized polypeptide can be extracted from the resin powder (e.g., with about 25% w/v acetic acid). Following the synthesis of the mGRFT tandemer constructs, further purification (e.g., using HPLC) optionally can be preformed in order to eliminate any incomplete proteins, polypeptides, peptides or free amino acids. Amino acid and/or HPLC analysis can be performed on the synthesized polypeptide to validate its identity. For other applications according to the invention, it may be preferable to produce the polypeptide as part of a larger fusion protein, either by chemical conjugation or through genetic means, such as are known to those skilled in the art. In this regard, the invention also provides a fusion protein comprising the isolated or purified mGRFT tandemer constructs and one or more other protein(s) having any desired properties or effector functions, such as cytotoxic or immunological properties, or other desired properties, such as to facilitate isolation, purification, analysis, or stability of the fusion protein.

The mGRFT tandemer constructs can be coupled to at least one effector component, which can be the same or different. The effector component can be polyethylene glycol, dextran, albumin, an immunological reagent, a toxin, an antiviral agent, or a solid support matrix. "Immunological reagent" will be used to refer to an antibody, an antibody fragment (e.g., an $F(ab')_2$, an Fab', an Fab, an Fv, an sFv, a dsFv, an eAd, or an Fc antibody fragment), an immunoglobulin, and an immunological recognition element. An immunological recognition element is an element, such as a peptide, e.g., the FLAG sequence that facilitates, through immunological recognition, isolation and/or purification and/or analysis of the protein or peptide to which it is attached. An immunological reagent also can be an immunogenic peptide, which can be fused to the mGRFT tandemers for enhancing an immune response.

In this respect, the invention provides an antiviral conjugate comprising the mGRFT tandemer construct bound to a virus or viral envelope glycoprotein. A fusion protein is a type of conjugate, wherein the mGRFT tandemer construct is coupled to one or more other protein(s) having any desired properties or effector functions, such as cytotoxic or immunological properties, or other desired properties, such as to facilitate isolation, purification or analysis of the fusion protein or increase the stability or in vivo half-life of the fusion protein. The mGRFT tandemer construct also can be attached to a chemical moiety which allows recognition, isolation, purification, and/or analysis of the protein or peptide. An example of such a chemical moiety is a His tag.

A "toxin" can be, for example, *Pseudomonas* exotoxin. An "antiviral agent" can be AZT, ddI, ddC, 3TC gancyclovir, fluorinated dideoxynucleosides, nevirapine, R82913, Ro 31-8959, BI-RJ-70, acyclovir, α-interferon, recombinant sCD4, michellamines, calanolides, nonoxynol-9, gossypol and derivatives thereof, gramicidin, amantatadine, rimantadine, and neuraminidase inhibitors, cyanovirin-N or a functional homolog or derivative thereof (see, for example, U.S. Pat. No. 5,843,882), or scytovirin or a functional homolog or derivative thereof (see, e.g., U.S. Pat. Nos. 7,494,798 and 8,067,530). A "solid support matrix" can be a magnetic bead, a flow-through matrix, a sponge, a stent, a culture plate, or a matrix comprising a contraceptive device, such as a condom, diaphragm, cervical cap, vaginal ring or contraceptive sponge. In an alternative embodiment, a solid support matrix can be an implant for surgical implantation in a host and, if appropriate, later removal.

Conjugates furthermore can comprise the mGRFT tandemer construct coupled to more than one effector molecule, each of which, optionally, can have different effector functions (e.g., such as a toxin molecule (or an immunological reagent) and a polyethylene glycol (or dextran or albumin) molecule). Diverse applications and uses of functional proteins and peptides attached to or immobilized on a solid support matrix, are exemplified more specifically for poly (ethylene glycol) conjugated proteins or peptides in a review by Holmberg et al. (In *Poly(Ethylene Glycol) Chemistry. Biotechnical and Biomedical Applications*, Harris, ed., Plenum Press: New York (1992), pp. 303-324).

The invention also provides isolated and purified nucleic acid molecules and synthetic nucleic acid molecules, which comprise a coding sequence for the inventive mGRFT tandemer constructs or fusion proteins or conjugates thereof.

Using an appropriate nucleic acid (e.g., DNA) coding sequence, the inventive mGRFT tandemer constructs or fusion proteins or conjugates thereof can be made by genetic engineering techniques (for general background see, e.g., Nicholl, in *An Introduction to Genetic Engineering*, Cambridge University Press: Cambridge (1994), pp. 1-5 & 127-130; Steinberg et al., in *Recombinant DNA Technology Concepts and Biomedical Applications*, Prentice Hall: Englewood Cliffs, N.J. (1993), pp. 81-124 & 150-162; Sofer in *Introduction to Genetic Engineering*, Butterworth-Heinemann, Stoneham, Mass. (1991), pp. 1-21 & 103-126; Old et al., in *Principles of Gene Manipulation*, Blackwell Scientific Publishers: London (1992), pp. 1-13 & 108-221; and Emtage, in *Delivery Systems for Peptide Drugs*, Davis et al., eds., Plenum Press: New York (1986), pp. 23-33). For example, DNA encoding the inventive mGRFT tandemer constructs or fusion proteins or conjugates thereof can be incorporated into an appropriate expression vector and delivered into an appropriate polypeptide-synthesizing organism (e.g., *E. coli, S. cerevisiae, P. pastoris*, or other bacterial, yeast, insect, plant or mammalian cells), where the DNA, under the control of an endogenous or exogenous promoter, can be appropriately transcribed and translated. Alternatively, the expression vector can be administered to a plant or animal, for example, for large-scale production (see, e.g., Fischer et al., *Transgenic Res.,* 9(4-5): 279-299 (2000); Fischer et al., *J. Biol. Regul. Homeost. Agents,* 14: 83-92 (2000); deWilde et al., *Plant Molec. Biol.,* 43: 347-359 (2000); Houdebine, *Transgenic Research,* 9: 305-320 (2000); Brink et al., *Theriogenology,* 53: 139-148 (2000); Pollock et al., *J. Immunol. Methods,* 231: 147-157 (1999); Conrad et al., *Plant Molec. Biol.,* 38: 101-109 (1998); Staub et al., *Nature Biotech.,* 18: 333-338 (2000); McCormick et al., *PNAS USA,* 96: 703-708 (1999); Zeitlin et al., *Nature Biotech.,* 16: 1361-1364 (1998); Tacker et al., *Microbes and Infection,* 1: 777-783 (1999); Tacket et al., *Nature Med.,* 4(5): 607-609 (1998); and *Methods in Biotechnology, Recombinant Proteins from Plants, Production and Isolation of Clinically Useful Compounds*, Cunningham and Porter, eds., Humana Press: Totowa, N.J. (1998)). Such expression vectors (including, but not limited to, phage, cosmid, viral, and plasmid vectors) are known to those skilled in the art, as are reagents and techniques appropriate for gene transfer (e.g., transfection, electroporation, transduction, micro-injection, transformation, etc.). If the inventive mGRFT tandemer construct is to be recombinantly produced in isolated eukaryotic cells or in a eukaryotic organism, such as a plant (see above references and also *Methods in Biotechnology, Recombinant Proteins from Plants, Production and Isolation of Clinically Useful Compounds*, Cunningham and Porter, eds., Humana Press: Totowa, N.J. (1998)), any glycosylation sites in the tandemer are rendered glycosylation resistant (e.g., the N-linked glycosylation sites at positions 45, 60, 71, and/or 104 relative to the amino acid sequence of griffitshsin (SEQ ID NO: 7) is rendered glycosylation-resistant, such as in accordance with the methods described herein. Subsequently, the recombinantly produced polypeptide can be isolated and purified using standard techniques known in the art (e.g., chromatography, centrifugation, differential solubility, isoelectric focusing, etc.), and assayed for antiviral activity.

In this regard, the invention also provides a vector comprising a nucleic acid sequence encoding an inventive mGRFT tandemer construct. The vector can be targeted to a cell-surface receptor if so desired. A nucleic acid molecule as described above can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology*, Vol. 153, Wu and Grossman, eds., Academic Press (1987)). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid as described above or a portion thereof ligated to a replication system functional in a prokaryotic or eukaryotic host cell. Replication systems can be derived from ColE1, 2 mμ plasmid, λ, SV40, bovine papilloma virus, and the like.

In addition to the replication system and the inserted nucleic acid, the construct of vectors can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

One of ordinary skill in the art will appreciate that any of a number of vectors known in the art are suitable for use in the invention. Suitable vectors include those designed for propagation and expansion or for expression or both. Examples of suitable vectors include, for instance, plasmids, plasmid-liposome complexes, and viral vectors, e.g., poxviral vectors, parvoviral-based vectors (i.e., adeno-associated virus (AAV)-based vectors), retroviral vectors, herpes simplex virus (HSV)-based vectors, and adenovirus-based vectors. Any of these expression constructs can be prepared using standard recombinant DNA techniques described in, e.g., Sambrook et al., *Molecular Cloning: A Laboratory Manual, 2nd edition*, Cold Spring Harbor Laboratory Press, Cold Spring Harbor, N.Y. (1989); Ausubel et al., *Current Protocols in Molecular Biology*, Greene Publishing Associates and John Wiley & Sons, New York, N.Y. (1994); Fischer et al., *Transgenic Res.,* 9(4-5): 279-299 (2000); Fischer et al., *J. Biol. Regul. Homeost. Agents,* 14: 83-92 (2000); deWilde et al., *Plant Molec. Biol.,* 43: 347-359 (2000); Houdebine, *Transgenic Research,* 9: 305-320 (2000); Brink et al., *Theriogenology,* 53: 139-148 (2000); Pollock et al., *J. Immunol. Methods,* 231: 147-157 (1999); Conrad et al., *Plant Molec. Biol.,* 38: 101-109 (1998); Staub et al., *Nature Biotech.,* 18: 333-338 (2000); McCormick et al., *PNAS USA,* 96: 703-708 (1999); Zeitlin et al., *Nature Biotech.,* 16: 1361-1364 (1998); Tacker et al., *Microbes and Infection,* 1: 777-783 (1999); and Tacket et al., *Nature Med.,* 4(5): 607-609 (1998). Examples of cloning vectors include the pUC series, the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Bacteriophage vectors, such as λGT10, λGT11, λZapII (Stratagene), λ EMBL4, and λ NM1149, also can be used. Examples of plant expression vectors include pBI101, pBI1, pBI01.2, pBI101.3, pBI121 and pBIN19 (Clonetech, Palo Alto, Calif.). Examples of animal expression vectors include pEUK-C1, pMAM and pMAMneo (Clonetech). When the vector is a plasmid (e.g. DNA plasmid), the plasmid can be complexed with chitosan.

When the vector is for administration to a host (e.g., human), the vector preferably has a low replicative efficiency in a target cell (e.g., no more than about 1 progeny per cell or, more preferably, no more than 0.1 progeny per cell are produced). Replication efficiency can readily be determined empirically by determining the virus titer after infection of the target cell.

An expression vector can comprise a native or nonnative promoter operably linked to an isolated or purified nucleic acid as described above. The selection of promoters, e.g., strong, weak, inducible, tissue-specific and developmental-specific, is within the skill in the art. Similarly, the combining of a nucleic acid molecule as described above with a promoter is also within the skill in the art.

The nucleic acid molecule, whether isolated and purified or synthetic, or cDNA encoding the mGRFT tandemer construct can be subcloned as part of a gene fusion. In a transcriptional gene fusion, the DNA or cDNA will contain its own control sequence directing appropriate production of protein (e.g., ribosome binding site, translation initiation codon, etc.), and the transcriptional control sequences (e.g., promoter elements and/or enhancers) will be provided by the vector. In a translational gene fusion, transcriptional control sequences as well as at least some of the translational control sequences (i.e., the translational initiation codon) will be provided by the vector. In the case of a translational gene fusion, a chimeric protein will be produced.

Nucleic acid molecules also can be constructed for specific fusion proteins containing the mGRFT tandemer construct plus a fusion component conferring additional desired attribute(s) to the composite protein. For example, a fusion sequence for a toxin or immunological reagent can be added to facilitate purification and analysis of the functional protein.

Nucleic acid molecules (e.g., genes) can be specifically constructed to code for fusion proteins, which contain the mGRFT tandemer construct coupled to an effector protein, such as a toxin or immunological reagent, for specific targeting to a virus or viral-infected cells, e.g., HIV and/or HIV-infected cells. In these instances, the mGRFT tandemer construct serves not only as a neutralizing agent but also as a targeting agent to direct the effector activities of these molecules selectively against a given virus, such as HIV or influenza. Thus, for example, a therapeutic agent can be obtained by combining the HIV-targeting function or influenza-targeting function of a functional the mGRFT tandemer construct with a toxin aimed at neutralizing infectious virus and/or by destroying cells producing infectious virus, such as HIV or influenza. Similarly, a therapeutic agent can be obtained, which combines the viral-targeting function of the mGRFT tandemer construct with the multivalency and effector functions of various immunoglobulin subclasses.

Viral-targeted conjugates can be prepared either by genetic engineering techniques (see, for example, Chaudhary et al. (1988), supra) or by chemical coupling of the targeting component with an effector component. The most feasible or appropriate technique to be used to construct a conjugate or fusion protein comprising the mGRFT tandemers will be selected based upon consideration of the characteristics of the particular effector molecule selected for coupling to the mGRFT tandemer construct. For example, with a selected non-proteinaceous effector molecule, chemical coupling, rather than genetic engineering techniques, may be the only feasible option for creating the desired conjugate.

An isolated cell comprising the mGRFT tandem construct, fusion protein, conjugate, nucleic acid molecule, or vector is also provided. Any suitable cell can be used. Examples include host cells, such as $E.$ $coli$ (e.g., $E.$ $coli$ Tb-1, TG-2, DH5α, XL-Blue MRF' (Stratagene), SA2821, and Y1090), $Bacillus$ $subtilis,$ $Salmonella$ $typhimurium,$ $Serratia$ $marcescens,$ $Pseudomonas$ (e.g., $P.$ $aerugenosa$), $N.$ $grassa$, insect cells (e.g., Sf9, Ea4), yeast ($S.$ $cerevisiae$) cells, and cells derived from a mammal, including human cell lines. Specific examples of suitable eukaryotic cells include VERO, HeLa, 3T3, Chinese hamster ovary (CHO) cells, W138 BHK, COS-7, and MDCK cells. Alternatively and preferably, cells from a mammal, such as a human, to be treated in accordance with the methods described herein can be used as host cells. In one embodiment, the cell is a human B cell.

The cell can be a mammalian cell, bacterium, or yeast. A preferred bacterium is lactobacillus or other commensal microorganism. The above-described nucleic acid molecule, optionally in the form of a vector, can be introduced into a host cell using such techniques as calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, and electroporation (see, e.g., Sambrook et al., supra, Davis et al., $Basic$ $Methods$ $in$ $Molecular$ $Biology$ (1986), and Neumann et al., $EMBO$ $J.$ 1, 841 (1982)). Desirably, the cell comprising the vector or nucleic acid expresses the mGRFT tandem construct, fusion protein, or conjugate such that the nucleic acid sequence is transcribed and translated efficiently by the cell.

The mGRFT tandem construct, fusion protein, conjugate, nucleic acid molecule, vector, or cell can be isolated. The term "isolated" as used herein encompasses compounds or compositions that have been removed from a biological environment (e.g., a cell, tissue, culture medium, body fluid, etc.) or otherwise increased in purity to any degree (e.g., isolated from a synthesis medium). Isolated compounds and compositions, thus, can be synthetic or naturally produced.

The invention further provides a composition comprising (i) the mGRFT tandem construct, fusion protein, conjugate, nucleic acid molecule, vector, or cell and (ii) a carrier, excipient or adjuvant therefor. Preferably, component (i) of the composition is present in an antiviral effective amount and the carrier is pharmaceutically acceptable. By "antiviral effective amount" is meant an amount sufficient to inhibit the infectivity of the virus.

The carrier can be any of those conventionally used and is limited only by chemico-physical considerations, such as solubility and lack of reactivity with the active agent of the invention, and by the route of administration. It is preferred that the pharmaceutically acceptable carrier be one which is chemically inert to the active agent and one which has no detrimental side effects or toxicity under the conditions of use. The pharmaceutically acceptable carriers described herein, for example, vehicles, adjuvants, excipients, and diluents, are well-known to those ordinarily skilled in the art and are readily available to the public. Typically, the composition, such as a pharmaceutical composition, can comprise a physiological saline solution; dextrose or other saccharide solution; or ethylene, propylene, polyethylene, or other glycol. The pharmaceutical composition preferably does not comprise mannose or N-acetyl-glucosamine, as these molecules may interfere with the functioning of the active agent.

If the composition is to be used to induce an immune response, it comprises an immune response-inducing amount of the mGRFT tandem construct, fusion protein, conjugate, nucleic acid molecule, vector, or cell and can further comprise an immunoadjuvant, such as polyphosphazene polyelectrolyte.

The composition can further comprise at least one additional active agent, such as an antiviral agent, in an antiviral effective amount. Suitable antiviral agents include AZT, ddA, ddI, ddC, 3TC gancyclovir, fluorinated dideoxynucleosides, acyclovir, α-interferon, nonnucleoside analog compounds, such as nevirapine (Shih et al., $PNAS,$ 88: 9878-9882, (1991)), TIBO derivatives, such as R82913 (White et al., $Antiviral$ $Res.,$ 16: 257-266 (1991)), Ro31-8959, BI-RJ-70 (Merigan, $Am.$ $J.$ $Med.,$ 90 (Suppl.4A): 8S-17S (1991)), michellamines (Boyd et al., $J.$ $Med.$ $Chem.,$ 37: 1740-1745 (1994)) and calanolides (Kashman et al., $J.$ $Med.$ $Chem.,$ 35: 2735-2743 (1992)), nonoxynol-9, gossypol and derivatives, gramicidin, Enfurtide (i.e., T20), cyanovirin-N and functional homologs thereof (Boyd et al. (1997), supra and U.S. Pat. No. 5,843,882), or scytovirin or a functional homolog or derivative thereof (see, e.g., U.S. Pat. Nos. 7,494,798 and 8,067,530). Other exemplary antiviral compounds include protease inhibitors (see R. C. Ogden and C. W. Flexner, eds., $Protease$ $Inhibitors$ $in$ $AIDS$ $Therapy$, Marcel Dekker, NY (2001)), such as saquinavir (see I. B. Duncan and S. Redshaw, in R. C. Ogden and C. W. Flexner, supra, pp. 27-48), ritonavir (see D. J. Kempf, in R. C. Ogden and C. W. Flexner, supra, pp. 49-64), indinavir (see B. D. Dorsey and J. P. Vacca, in R. C. Ogden and C. W. Flexner, supra, pp. 65-84), nelfinavir (see S. H. Reich, in R. C. Ogden and C. W. Flexner, supra, pp. 85-100), amprenavir (see R. D. Tung, in R. C. Ogden and C. W. Flexner, supra, pp. 101-118), tenofovir (see Ferir et al., $Virology,$ 417(2): 253-258 (2011)), maraviroc (see Ferir et al., $Virology,$ 417(2): 253-258 (2011)), carbohydrate binding agents (see Ferir et al., $AIDS$ $Res.$ $Hum.$ $Retrovir.,$ 28(11): 1513-23 (2012)), and anti-TAT agents. If the composition is to be used to induce an immune response, it comprises an immune response-inducing amount of the inventive agent and can further comprise an immunoadjuvant, such as polyphosphazene polyelectrolyte.

The composition (e.g., pharmaceutical composition) can contain other pharmaceuticals, such as virucides, immunomodulators, immunostimulants, antibiotics and absorption enhancers. Exemplary immunomodulators and immunostimulants include various interleukins, sCD4, cytokines, antibody preparations, blood transfusions, and cell transfusions. Exemplary antibiotics include antifungal agents, antibacterial agents, and anti-*Pneumocystitis carnii* agents. Exemplary absorption enhancers include bile salts and other surfactants, saponins, cyclodextrins, and phospholipids (Davis (1992), supra).

The mGRFT tandem construct, fusion protein, conjugate, nucleic acid molecule, vector, cell, or composition can be used to inhibit a broad range of viruses (see, e.g., *Principles of Virology: Molecular Biology, Pathogenesis, and Control*, Flint et al., eds., ASM Press: Washington, D.C. (2000), particularly Chapter 19). Examples of viruses that may be treated in accordance with the invention include, but are not limited to, Type C and Type D retroviruses, HTLV-1, HTLV-2, HIV, FIV, FLV, SIV, MLV, BLV, BIV, equine infectious virus, anemia virus, Japanese encephalitis (see, e.g., Ishag et al, *Arch. Virol.*, 158(2): 349-58 (2013)), avian sarcoma viruses, such as Rous sarcoma virus (RSV), hepatitis type A, B, C, non-A and non-B viruses, arboviruses, varicella viruses, herpes viruses (e.g., HHV-6, HSV-1, and HSV-2 (see, e.g., Nixon et al., *J. Virol.*, 87(12): doi: 10.1128/JVI.00012-13 (2013)), measles, mumps, filovirus (e.g., Ebola, such as Ebola strains Sudan, Zaire, Cote d'Ivoire, and Reston), human and animal coronavirus (e.g., SARS virus), and rubella viruses. The inventive mGRFT tandem construct, fusion protein, conjugate, nucleic acid molecule, vector, or cell also can be used to inhibit influenza viral infection, such as an H5N1 viral infection, i.e., a Bird flu viral infection, (see, e.g., *Fields Virology*, third edition, Fields et al., eds., Lippincott-Raven Publishers: Philadelphia, Pa. (1996), particularly Chapter 45) prophylactically and therapeutically in accordance with the methods set forth herein.

The inventive mGRFT tandem construct, fusion protein, conjugate, nucleic acid molecule, vector, cell, or composition thereof can be administered to any host (e.g., mammal, preferably a human) in need thereof. As a result of administration of mGRFT tandem construct, fusion protein, conjugate, nucleic acid molecule, vector, or cell to the mammal, infection of the mammal by a virus (e.g., HIV) is inhibited. The inventive method can prophylactically or therapeutically inhibit infection by any type of virus (e.g., HIV), but preferably inhibits an HIV infection, such as an HIV-1 and/or HIV-2 infection. The inventive method can be used to inhibit infection by any HIV group (e.g., groups M and/or O), and subtype (e.g., clades A, B, C, D, E, EA, F, and/or G).

When provided therapeutically, the mGRFT tandem construct, fusion protein, conjugate, nucleic acid molecule, vector, cell or composition thereof is provided at or after the diagnosis of a viral (e.g., HIV) infection.

When provided prophylactically (e.g., as a topical microbicide agent in the form of a film or solid suppository), the mGRFT tandem construct, fusion protein, conjugate, nucleic acid molecule, vector, cell or composition thereof is provided in advance of a viral (e.g., HIV) infection, such as to patients or subjects who are at risk for being exposed to a virus (e.g., HIV) or who have been newly exposed to a virus (e.g., HIV). If the virus is HIV, then the patients or subjects include healthcare workers, fetuses, neonates, or infants (e.g., nursing infants) whose mothers are infected or at risk for being infected, intravenous drug users, recipients of blood transfusions, blood products, or transplantation tissue, and other individuals who have been exposed to a body fluid that contains or may contain HIV. The prophylactic administration of the mGRFT tandem construct, fusion protein, conjugate, nucleic acid molecule, vector, or cell or composition thereof prevents, ameliorates, or delays viral (e.g., HIV) infection. In subjects who have been newly exposed to the virus but who have not yet displayed the presence of the virus (as measured by PCR or other assays for detecting the virus) in blood or other body fluid, efficacious treatment with the mGRFT tandem construct, fusion protein, conjugate, nucleic acid molecule, vector, or cell or composition thereof partially or completely inhibits or delays the appearance of the virus or minimizes the level of the virus in the blood or other body fluid of the exposed individual.

The invention provides a method of inhibiting prophylactically or therapeutically a viral infection, in particular an influenza viral infection or HIV infection, of a host. The method comprises administering to the host an effective amount of the inventive mGRFT tandem construct, fusion protein, conjugate, nucleic acid molecule, vector, or cell or composition thereof (herein referred to as "the inventive antiviral agent"). When the viral infection is an influenza viral infection and the inventive antiviral agent is administered topically to the host, preferably the inventive antiviral agent is administered to the respiratory system of the host, preferably as an aerosol or microparticulate powder.

The prophylactic and therapeutic treatment of many viral infections, including influenza virus infections, is complicated by appearance of virus forms resistant to currently employed medications, such as neurominidase inhibitors. The inventive method is particularly useful in this context, as the inventive antiviral agent binds a wide range of glycoproteins present on the viral surface. Accordingly, the inventive antiviral agent can be administered to an animal, preferably a human, dog, cat, bird, cow, pig, horse, lamb, mouse, or rat, in combination with other antiviral agents to guard against the propagation of antiviral-resistant strains of virus. In addition, it is thought that during adaptive mutation (e.g., resistance to neuraminidase inhibitors), the level of glycosylation found at the viral surface increases in some viruses, such as influenza. Thus, in that the inventive antiviral agent binds sugars of viral surface glycoproteins, the inventive method provides a valuable complimentary therapy to current antiviral regimens.

One skilled in the art will appreciate that various routes of administering a drug are available, and, although more than one route can be used to administer a particular drug, a particular route can provide a more immediate and more effective reaction than another route. For example, the antiviral agent of the invention can be inhaled in methods of prophylactically treating a subject for influenza infection. Delivery of the antiviral agent to a location of initial viral contact, such as the nose or mouth, blocks the onset of infection. The antiviral agent can be administered via subcutaneous injection. Alternatively, in acute or critical medical situations, the antiviral agent can be administered intravenously. In many cases of infection, a patient generates an immune response to a virus. However, the effects of the viral infection so severely compromise the health of the patient that an effective immune response is not reached prior to death. Administration of the antiviral agent can prolong the life of the patient until a patient's natural immune defense clears the virus.

Formulations suitable for oral administration can consist of liquid solutions, such as an effective amount of the compound dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present invention from degradation within the gastrointestinal tract (see, for example, Wallace et al., *Science,* 260: 912-915 (1993)).

The antiviral agent of the invention, alone or in combination with other antiviral compounds, can be made into aerosol formulations or microparticulate powder formulations to be administered via inhalation. These aerosol formulations can be placed into pressurized acceptable propellants, such as dichlorodifluoromethane, propane, nitrogen, and the like.

The antiviral agent of the invention, alone or in combinations with other antiviral compounds or absorption modulators, can be made into suitable formulations for transdermal application and absorption, such as a patch (Wallace et al. (1993), supra). Transdermal electroporation or iontophoresis also can be used to promote and/or control the systemic delivery of the compounds and/or compositions of the present invention through the skin (e.g., see Theiss et al., *Meth. Find. Exp. Clin. Pharmacol.,* 13: 353-359 (1991)).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, gels and the like containing, in addition to the active ingredient, such as, for example, freeze-dried lactobacilli or live lactobacillus cultures genetically engineered to directly produce a construct, fusion protein, or conjugate of the present invention, such carriers as are known in the art. Topical administration is preferred for the prophylactic and therapeutic treatment of influenza viral infection, such as through the use of an inhaler, for example.

Formulations for rectal administration can be presented, for example, as a film formulation or suppository with a suitable base comprising, for example, cocoa butter or a salicylate. Formulations suitable for vaginal administration can be presented as film formulations, vaginal ring formulations, pessaries, tampons, creams, gels, pastes, foams, or spray formulas containing, in addition to the active ingredient, such as, for example, freeze-dried lactobacilli or live lactobacillus cultures genetically engineered to directly produce a construct, fusion protein, or conjugate of the present invention, such carriers as are known in the art to be appropriate. Similarly, the active ingredient can be combined with a lubricant as a coating on a condom. Indeed, preferably, the active ingredient is applied to any contraceptive device, including, but not limited to, a condom, a diaphragm, a cervical cap, a vaginal ring, and a sponge, wherein the device is not limited to administration as a contraceptive.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

Formulations comprising a construct, fusion protein, or conjugate suitable for virucidal (e.g., HIV) sterilization of inanimate objects, such as medical supplies or equipment, laboratory equipment and supplies, instruments, devices, and the like, can, for example, be selected or adapted as appropriate, by one skilled in the art, from any of the aforementioned compositions or formulations. In that respect, the invention provides a method of inhibiting a virus in a biological sample or in/on an inanimate object comprising contacting the biological sample or the inanimate object with a viral-inhibiting amount of the inventive construct, conjugate, nucleic acid, vector, cell, or composition, which method optionally further comprises the prior, simultaneous, or subsequent contacting of the biological sample or inanimate object with an antiviral agent or another agent that is efficacious in inhibiting the virus.

It will also be appreciated by one skilled in the art that a DNA sequence of the mGRFT construct, conjugate, or fusion protein of the invention can be inserted ex vivo into mammalian cells previously removed from a given animal, in particular a human, host. Such cells can be employed to express the corresponding mGRFT construct, conjugate, or fusion protein in vivo after reintroduction into the host. Feasibility of such a therapeutic strategy to deliver a therapeutic amount of an agent in close proximity to the desired target cells and pathogens, i.e., virus, more particularly retrovirus, specifically HIV and its envelope glycoprotein gp120, has been demonstrated in studies with cells engineered ex vivo to express sCD4.

It is also possible that, as an alternative to ex vivo insertion of the DNA sequence of the mGRFT construct, conjugate, or fusion protein of the invention, such a sequence can be inserted into cells directly in vivo, such as by use of an appropriate viral vector. Such cells transfected in vivo are expected to produce antiviral amounts of the mGRFT construct, conjugate, or fusion protein directly in vivo.

Alternatively, a DNA sequence corresponding to the mGRFT construct, conjugate, or fusion protein can be inserted into suitable nonmammalian host cells, and such host cells will express therapeutic or prophylactic amounts of the mGRFT construct, conjugate, or fusion protein directly in vivo within or onto a desired body compartment of an animal, in particular a human. In a preferred embodiment of the present invention, a method of female-controllable prophylaxis against viral infection, such as HIV infection, comprises the intravaginal administration and/or establishment of, in a female human, a persistent intravaginal population of lactobacilli that have been transformed with a coding sequence of the present invention to produce, over a prolonged time, effective virucidal levels of a the mGRFT construct, conjugate, or fusion protein, directly on or within or onto the vaginal and/or cervical and/or uterine mucosa.

One of ordinary skill can determine the effectiveness of the composition to inhibit a viral infection (e.g., by inducing an immune response against the virus) using routine methods known in the art. Cell-mediated response can be determined by employing, for example, a virus antigen-stimulated T-cell proliferation assay. The presence of a humoral immune response can be determined, for instance, with the Enzyme Linked Immunosorbent Assay (ELISA). The skilled artisan will appreciate that there are numerous other suitable assays for evaluating induction of an immune response. To the extent that a dose is inadequate to induce an appropriate immune response, "booster" administrations can subsequently be administered in order to prompt a more effective immune response.

The pre-binding of GRFT to HIV gp120 envelope protein has been shown to increase the immunogenicity of the envelope glycoprotein when GRFT and HIV gp120 envelope protein are administered as a vaccine (see, e.g., Banerjee et al, *AIDS Res. Hum. Retrovir.,* 28(2): 206-214 (2012)). Therefore, in one aspect of the invention, the mGRFT tandem construct, fusion protein, conjugate, nucleic acid molecule, vector, cell or composition thereof is administered with HIV gp120 envelope glycoprotein.

Since the effective level is used as the preferred endpoint for dosing, the actual dose and schedule can vary, depending upon interindividual differences in pharmacokinetics, drug distribution, and metabolism. The "effective level" can be defined, for example, as the blood or tissue level (e.g., 0.1-1000 nM) desired in the patient that corresponds to a concentration of the mGRFT tandem construct, fusion protein, conjugate, nucleic acid molecule, vector, cell, or composition thereof, which inhibits a virus, such as HIV, in an assay known to predict for clinical anti-viral activity of chemical compounds and biological agents. The "effective level" for agents of the invention also can vary when the mGRFT tandem construct, fusion protein, conjugate, nucleic acid molecule, vector, cell, or composition thereof, is used in combination with AZT or other known anti-viral compounds or combinations thereof.

One skilled in the art can easily determine the appropriate dose, schedule, and method of administration for the exact formulation of the composition being used, in order to achieve the desired effective concentration in the individual patient. One skilled in the art also can readily determine and use an appropriate indicator of the "effective concentration" of the mGRFT tandem construct, fusion protein, conjugate, nucleic acid molecule, vector, cell, or composition thereof of the invention by a direct (e.g., analytical chemical analysis) or indirect (e.g., with surrogate indicators such as p24 or RT) analysis of appropriate patient samples (e.g., blood and/or tissues).

The inventive methods can further comprise concurrent, pre- or post-treatment with an adjuvant to enhance the immune response, such as the prior, simultaneous or subsequent administration, by the same or a different route, of an antiviral agent or another agent that is efficacious in inducing an immune response to the virus, such as an immunostimulant. See, for example, Harlow et al. (1988), supra.

The antiviral, e.g., anti-HIV, activity of the mGRFT tandem construct, fusion protein, conjugate, nucleic acid molecule, vector, cell or composition thereof of the invention can be further demonstrated in a series of interrelated in vitro anti-viral assays (Gulakowski et al., *J. Virol. Methods,* 33: 87-100 (1991)), which accurately predict for anti-viral activity in humans. These assays measure the ability of compounds to prevent the replication of HIV and/or the cytopathic effects of HIV on human target cells. These measurements directly correlate with the pathogenesis of HIV-induced disease in vivo.

The following examples further illustrate the invention but, of course, should not be construed as in any way limiting its scope.

Example 1

This example demonstrates the materials and methods for Examples 2-6.

Cloning, Expression and Purification of dGRFT, mGRFT and GRFT Tandemers

All restriction enzymes were purchased from New England Biolabs. All chemicals were obtained from American Bioanalytical, unless otherwise stated. All primers were purchased from Integrated DNA Technologies.

The GRFT monomer 1GS-S(PDB ID 3LL2) was chosen as the repeating unit in the design of mGRFT tandemers, primarily since an L2S mutation at the N-terminus of 1GS-S rendered this monomer more susceptible to proteolytic cleavage of its N-terminal affinity tag. Furthermore, this mGRFT construct was more stable than other tested versions, such as 1GS-SDNAY (Moulaei et al., *Structure,* 18(9): 1104-15 (2010)).

Although purification of tandemers was preformed as described previously in Moulaei et al., *Structure,* 18(9): 1104-15 (2010), several methods for increasing efficiency and yield were explored. All GRFT tandemers were expressed in BL21(DE3)pLysS cell line. Inclusion of 50 mM maltose or 20% glycerol in the lysis buffer increased the protein yield, presumably by dissociating the tandemers from bacterial cell wall debris. The lysate could be further purified by heating at 50° C. for 15 minutes, or adjusting the lysis buffer with 15% v/v ethanol or 10% v/v isopropanol. The tandemers, GRFT, and mGRFT are stable in these conditions. Individual tandemers, the number of monomeric units, the type of linkers, and selected physical properties are listed in Table 1.

TABLE 1

GRFT Tandemer Properties.

| Name | Number of domains | Linker | Molecular Weight (kDa) | Anti-HIV $EC_{50}$ (pM) | Terminal Binding Surface Distance (Å) |
|---|---|---|---|---|---|
| GRFT | 2 | none | 25.6 | 13.8 ± 0.3 | 50 |
| mGRFT (1GS-S)* | 1 | none | 12.8 | 119,300 ± 19,300 | n.a. |
| 2mGRFT | 2 | Gly-Thr-Gly | 25.8 | 2.7 ± 2.7 | 70 |
| 2mGRFT3 | 2 | $(Gly-Thr-Gly)_3$ | 26.2 | 2.6 ± 5.3 | 90 |
| 3mGRFT | 3 | Gly-Thr-Gly | 38.8 | 1.0 ± 2.9 | 90 |
| 4mGRFT | 4 | Gly-Thr-Gly | 51.8 | 1.2 ± 0.3 | 100 |

*Zeitlin et al., *Proc. Natl. Acad. Sci.*, 106: 6029-6030 (2009)

Construction of Plasmid p420TG and p2mGRFT

An expression vector containing the gene for 1GS-S downstream of a TEV protease cleavage site (Moulaei et al., *Structure,* 18(9): 1104-15 (2010)) was used as a template to amplify a second 1GS-S cassette using a standard PCR protocol and PfuUltra® Hotstart PCR Master Mix (Stratagene). The amplified cassette contained only the 1GS-S gene terminated with a stop codon and flanked by two XhoI restriction endonuclease sites. The amplified 1GS-S cassette was inserted at the XhoI site downstream of the first 1 GS-S cassette in the original expression vector used as a template. The correct orientation of the second cassette was verified by sequencing. Site-directed mutagenesis was used to mutate the DNA sequence between the two 1GS-S cassettes to 5'-ggtaccgcgggctagcatatgtcgaccggt-3' (SEQ ID NO: 1), removing the stop codon at the 3'-terminus of the first 1GS-S cassette and introducing a new multiple-cloning site (MCS) with flanking KpnI and AgeI sites. In order to create an expression plasmid for 2mGRFT (p2mGRFT), site-directed mutagenesis was used to alter the MCS in p420TG to 5'-ggtacaggt-3'. The resulting vector contained a single ORF expressing two 1 GS-S domains preceded by a TEV protease cleavage site and linked by a GlyThrGly linker.

Construction of Plasmids p3m GRFT, p4m GRFT, and p2n GRFT$^{long}$

Primers KpnIGly-mGRFT (5'-ggggtaccggcagctcgac-ccatcgcaag-3'; SEQ ID NO: 2) and AgeIGly-mGRFT (5'-ggaccggtgccgtactgttcatagtagatgtcaggctatc-3'; SEQ ID NO: 3) were used with p2mGRFT as a template in a standard PCR reaction. Two amplicons corresponding to a single and a double 1GS-S cassette were separated and purified from an agarose gel. Each amplicon contained a KpnI site followed by a glycine codon (ggc) at the 5' terminus and the same glycine codon followed by a AgeI site at the 3' terminus. The single and double 1GS-S cassettes were ligated in between the KpnI and AgeI sites in p420TG to yield p3mGRFT and p4mGRFT, respectively. Site-directed mutagenesis was used to alter the GlyThrGly linker in p2mGRFT to a GlyThrGlyGlyThrGlyGlyThrGly (SEQ ID NO: 5) linker yielding p2mGRFT$^{long}$ for expression of 2mGRFT$^{long}$.

The complete nucleic acid and amino acid sequence of the GRFT tandemers indicated in Table 2.

TABLE 2

GRFT Tandemer Sequences.

| GRFT Tandemer | | SEQ ID NO |
|---|---|---|
| 2mGRFT (2mG) | DNA | 8 |
| (mGRFT-GlyThrGly-mGRFT) | Amino Acid | 9 |
| 3mGRFT (3mG) | DNA | 10 |
| (mGRFT-GlyThrGly-mGRFT-GlyThrGly-mGRFT) | Amino Acid | 11 |
| 4mGRFT (4mG) | DNA | 12 |
| (mGRFT-GlyThrGly-mGRFT-GlyThrGly-mGRFT-GlyThrGly-mGRFT) | Amino Acid | 13 |
| 2mGRFT$^{long}$ (2mG3) | DNA | 14 |
| (mGRFT-GlyThrGlyGlyThrGlyGlyThrGly-mGRFT) | Amino Acid | 15 |

Differential Scanning Calorimetry

Differential scanning calorimetry (DSC) experiments were carried out on a Microcal VP-DSC microcalorimeter (Microcal, Northampton, Mass.). The concentrations of all tandemer proteins were determined by amino acid analysis, and a 60 M concentrated sample of a tandemer protein was evaluated per experiment. By routine protocol, buffer (50 mM Tris, 60 mM NaCl) was introduced to both the reference and sample cells and the calorimeter was allowed to ramp through one cycle of a heat-cool cycle (10° C. to 90° C.) at a heating/cooling rate of 60° C./hr. During the down scan at 25° C., the buffer solution from the sample cell was quickly and efficiently replaced with a degassed tandemer protein sample. The entire system was re-pressurized to approximately 30 psi of positive pressure to prevent evaporation at higher temperatures, and the experiment was allowed to continue. A total of 6 alternating up-down scans (10° C. to 90° C.) was performed to measure possible reversibility of folding/unfolding of the tandemers. According to manufacturing protocol, Origin DSC Analysis software was used to correct for buffer effects and to carry out the integration of the unfolding transitions of the tandemers. The baseline corrected thermograms were fitted to a two-state melting model and the calorimetric transition enthalpy ($\Delta H_{unf}$) was obtained from the area under the excess heat capacity peak, the midpoint of the transition calculated as the melting temperature (Tm).

Isothermal Titration Calorimetry

Isothermal titration calorimetry (ITC) experiments were performed on a Microcal VP-ITC microcaloorimeter (MicroCal, Northampton, Mass.). In a typical experiment with the tandemers and gp120, the tandemer protein (180 μM) was placed in the syringe injector and the gp120 was placed in the calorimeter cell (2.5 μM). In all experiments, a total of 55 injections of tandemer (5 μl/injection) were made, with 600 s spacing between injections. The titrations were all done in a rapidly stirring solution (300 rpm) held at a constant temperature of 30° C. The heats of binding were recorded as the excess power compensation required to maintain the same temperature during the course of the titration. Baseline experiments of tandemer titration into buffer were done to calculate heats of dilution and this value was subtracted from the experimental heats of binding. The resulting isotherms were fitted using Origin 5.0 nonlinear least-squares program according to manufacturer's protocol, and the values for the enthalpy of binding ($\Delta H$) and the dissociation constant were obtained. From the dissociation constant, a value for the free energy of binding ($\Delta G$) was extrapolated ($\Delta G=-RT\ln Ka$), and from this value, the entropy of binding ($\Delta S$) was lastly calculated ($\Delta G=\Delta H-T\Delta S$).

Whole-Cell Anti-HIV Bioassays

A 2,3-bis-[2-methoxy-4-nitro-5-sulfophenyl]-2H-tetrazolium-5-carboxanilide inner salt (XTT)-tetrazolium-based assay was used to determine the anti-HIV activity of mGRFT, GRFT, and GRFT tandemers against HIV-1$_{RF}$ challenged T-lymphoblastic CEM-SS cells as described previously (Gulakowski et al., J. Virol Methods, 33(1-2): 87-100 (1991)). CEM-SS cells were maintained in RPMI 1640 media without phenol red and supplemented with 5% fetal bovine serum (BioWhittaker), 2 mM L-glutamine (BioWhittaker), and 50 μg/ml gentamicin (BioWhittaker) (complete medium). Exponentially growing cells were washed and resuspended in complete medium, and a 50 μl aliquot containing 5×10$^3$ cells was added to individual wells of a 96-well round-bottom microtiter plate containing serial dilutions of dimeric GRFT, mGRFT or the GRFT tandemers (2mG, 2mG3, 3mG, 4mG) in a volume of 100 μl of medium.

Stock supernatants of HIV-1$_{RF}$ were diluted in complete medium to yield sufficient cytopathicity (80-90% cell kill in 6 days), and a 50 µl aliquot was added to appropriate wells. Plates were incubated for 6 days at 37° C. and then stained for cellular viability using XTT. All experiments were performed in triplicate.

Dynamic Light Scattering

Whole HIV-1 viruses (AIDS and Cancer Virus Program, SAIC-Frederick, Inc., Frederick National Laboratory for Cancer Research, Frederick, Md. 21702, USA) at stock concentration (~$10^{11}$ virions/mL) were diluted 1,000-fold in dilution buffer (10 mM Tris, 150 mM NaCl, 1 mM EDTA, pH 7.4), and 1 mL of this diluted virus volume was transferred to a plastic cuvette. Dilution was necessary to prevent complete scattering of the instrument laser. Autocorrelation measurements were carried out at 25° C. using a DynaPro NanoStar instrument (Wyatt Technology, Santa Barbara, Calif. 93117, USA) that provided particle size distributions, the peak of which was taken to be the mean particle size. For dynamic light scattering (DLS) experiments involving griffithins, the viruses were pre-mixed with lectin at the same concentrations used in cryo-electron microscopy experiments. This ensured a valid comparison between dynamic light scattering experiments, and the imaging experiments in which there was no sample dilution before mixing. Dynamic light scattering measurements were carried out with assistance from Dr. Grzegorz Piszczek (National Institutes of Health, National Heart, Lung and Blood Institute, Biophysics Facility, Bethesda, Md. 20814, USA).

Cryo-Electron Microscopy

Imaging experiments used purified suspensions of HIV-1 BaL virions with estimated concentration of ~$10^{11}$ virions/mL (AIDS and Cancer Virus Program, SAIC-Frederick, Inc., Frederick National Laboratory for Cancer Research, Frederick, Md. 21702, USA). Prior to receipt, viruses were inactivated with Aldrithiol-2 which preserves viral entry capacity and antigenic integrity at levels similar to those of untreated virus. Sample mixtures were prepared by adding 10 nm protein-A gold colloid (Cell Microscopy Center, Utrecht University, 3584 CH Utrecht, The Netherlands) to virus suspension, followed by addition of one of six griffithsin constructs and incubation at 4° C. for 30 min. All griffithsin constructs were added to the virion suspension at equimolar concentrations with respect to the griffithsin monomer. Two microliters of sample mixture were applied to plasma cleaned carbon-coated 200-mesh grids (Quantifoil Micro Tools, 07745 Jena, Germany) and immediately blotted and plunge frozen using a Mark III Vitrobot (FEI Company, Hillsboro, Oreg. 97124, USA) maintained at 25° C. and 100% humidity. Data was collected on samples maintained at −193° C. using a Tecnai G2 Polara transmission electron microscopy (FEI Company, Hillsboro, Oreg. 97124, USA) operated at 200 kV and equipped with an energy-filter and 2 K×2 K post-energy filter CCD camera (Gatan Incorporated, Pleasanton, Calif. 94588, USA). Projections were acquired with a 10-20 e$^-$/Å$^2$ dose at 4.5 k× magnification with −70 µm underfocus. Tilt series spanned an angular range of +/−65° with 20 tilt increments and were acquired at −2.5 m underfocus with a per-tilt dose of 1-2 e$^-$/Å$^2$. Tilt series were aligned using RAPTOR as implemented in IMOD (Amat et al., *J. Struct. Biol.*, 161(3): 260-275 (2008); Kremer et al., *J. Struct. Biol.*, 116(1): 71-76 (1996)), and tomograms were reconstructed using R-weighted back projection as implemented in IMOD.

Viruses, Envelope Clones, MAbs, Cell Lines and Lectins

HIV-1 subtype C isolates Du151, and Du179 were isolated in South Africa from individuals infected with HIV-1 subtype C (van Harmelen et al., *AIDS Res. Hum. Retroviruses*, 17(16): 1527-1531 (2001)). HIV-1 subtype C envelope clones Du151.2 and CAP206.08J were amplified from South African individuals at the acute or early stage of HIV infection (Gray et al., *J. Virol.*, 81(19): 10769-10776; Li et al., *J. Virol.*, 80(23): 11776-11790 (2006)). HIV-1 subtype B envelopes, CAAN5342.A2, QH0692.42 and PVO.4 were amplified from acutely infected individuals from the U.S.A, Trinidad and Tobago and Italy (Li et al., *J. Virol.*, 79(16): 10108-10125 (2005)). The pSG3Δenv plasmid was obtained from Beatrice Hahn. The mAb 2G12 was obtained from the NIH Reference and Reagent Program and the IAVI Neutralizing Antibody Consortium. The JC53bl-13 cell line was obtained from the NIH Reference and Reagent Program (Cat No 8129) and the 293T cell line was obtained from the American Type Culture Collection. Both cell lines were cultured in DMEM containing 10% fetal bovine serum (FBS) and were mycoplasma-free. Cell monolayers were disrupted at confluence by treatment with 0.25% trypsin in 1 mM EDTA.

Generation of Env-Pseudotyped Virus Stock

HIV-1 pseudoviruses were generated by co-transfection of the Env and pSG3Δenv plasmids (Wei et al., *Nature*, 422: 307-312 (2003)) into 293T cells using the Fugene transfection reagent (Roche Applied Science, Indianapolis, Ind.). The TCID$_{50}$ of each virus stock was quantified by infecting JC53bl-13 cells with serial 5-fold dilutions of the supernatant in quadruplicate in the presence of DEAE dextran (37.5 g/mL) (Sigma-Aldrich, St. Louis, Mo.). The Bright Glo™ Reagent (Promega, Madison, Wis.) was used to measure the infection after 48 hours of tissue culture, according to the manufacturer instructions. Luminescence was measured in a Wallac 1420 Victor Multilabel Counter (Perkin-Elmer, Norwalk, Conn.). The TCID$_{50}$ was calculated as described elsewhere (Johnson and Byington, *Techniques in HIV Research*. Adovini et al. eds. Stockton Press; New York, pp. 71-76 (1990)).

Single Cycle Neutralization Assay in JC53bl-13

The pseudovirus neutralization assay was carried out as described elsewhere (Montefiori, *Current Protocols in Immunology*. Coligan et al. eds. John Wiley & Sons, pp. 12:11.1-12:11.5 (2004)). Briefly, three-fold dilution series of each lectin in 100 µL of DMEM with 10% FBS (growth medium) were prepared in a 96-well plate in duplicate. Two hundred TCID$_{50}$ of pseudovirus in 50 µL of growth medium was added and the mixture was incubated for 1 hour at 37° C. Then 100 µL of JC53bl-13 at a concentration of 1×10$^5$ cells/mL of growth medium with 37.5 µg/mL of DEAE dextran was added to each well and cultured at 37° C. for 48 hours. Infection was evaluated by measuring the activity of the firefly luciferase. Titers were calculated as the inhibitory concentration that causes 50% reduction (IC$_{50}$) of relative light unit (RLU) compared to the virus control (wells with no inhibitor) after the subtraction of the background (wells without both the virus and the inhibitor).

Example 2

This example demonstrates the antiviral activity of the GRFT tandemers.

1GS-S(PDB ID 3LL2) was chosen as the repeating unit in the design of mGRFT tandemers. An L2S mutation at the N-terminus of 1GS-S rendered this monomer more susceptible to proteolytic cleavage of its N-temnninal affinity tag. Furthermore, this mGRFT construct was more stable than 1GS-SDNΔY (Moulaei et al., *Structure*, 18(9): 1104-15

(2010)). The structures of the GRFT, mGRFT, and the tandemers are depicted in schematic form in FIG. 1.

The GRFT tandemers were tested simultaneously with mGRFT and GRFT in a whole-cell anti-HIV assay that measures HIV-1$_{RF}$-induced cytopathicity in the T-lymphoblastic cell line CEM-SS. The results (see Table 1) showed that mGRFT was significantly weaker than GRFT, with an EC$_{50}$ value of 119.3 pM.

The GRFT tandemers all showed anti-HIV activity significantly better than mGRFT and five- to ten-fold better than native, dimeric GRFT (see Table 1). The 2mG (EC$_{50}$=2.7 pM) and 2mG3 (EC$_{50}$=2.6 pM) tandemers were 5-fold more active than GRFT (EC$_{50}$=13.8 pM). The antiviral activity displayed by the 3mG tandemer was enhanced by another 5 fold with an EC$_{50}$ of 1.0 pM. The anti-HIV activity of 4mG (EC$_{50}$=1.2 pM) was similar to that of 3mG, indicating that that there may be a limit to the possible enhancement of GRFT activity. The similar anti-HIV activity of 2mG and 2mG3 indicates that the longer interdomain linker did not affect the potency of the tandemers.

The maximum theoretical distance between the terminal carbohydrate-binding surfaces of each tandemer was calculated based on models derived from the X-ray crystal structure of mGRFT (see Table 1). In native GRFT the distance between the centers of the carbohydrate-binding regions on each domain was ~50 Å. Increasing the linear length of the tandemers from ~70 Å (2mG) to ~90 Å (2mG3) resulted in a nearly identical anti-HIV activity, suggesting that this increase in potential distance between mGRFT domains was not a determining factor in anti-HIV potency. Increasing the number of mGRFT domains did enhance antiviral activity. However, this effect was limited to three mGRFT domains as evidenced from the nearly identical anti-HIV activities of 3mG and 4mG (see Table 1). The limit on the number of mGRFT domains possibly was due to geometric constraints that could limit access to glycan ligands by the fourth mGRFT domain of 4mG and/or saturation of viral glycoproteins with mGRFT domains.

Example 3

This example describes dynamic light scattering analysis of the GRFT tandemers.

One of the common attributes of many lectins is their capacity to agglutinate cells. Though antiviral lectins, such as cyanovirin-N, scytovirin, and GRFT, have been shown not to agglutinate human cells, it has been suggested that these multi-binding domain lectins aggregate viruses.

To evaluate the role enhanced flexibility in binding domains may play in this phenomenon, dynamic light scattering was used to measure the aggregation of HIV-1$_{BAL}$ virions after treatment with mGRFT, dGRFT, or one of the four GRFT tandemers. Negative controls with buffer or purified protein alone did not measurably scatter light.

As shown in FIG. 2, dGRFT did aggregate HIV-1$_{BAL}$ virions to a significant extent when compared to untreated virions. As expected, mGRFT (with only one binding domain) did not aggregate virus. Interestingly, none of the GRFT tandemers, including 4mG with four binding domains, aggregated virus whatsoever.

The data presented here demonstrate that virion agglutination is not required for the anti-HIV potency of GRFT tandemers and hence, by GRFT itself. Native GRFT and mGRFT tandemers share the same mechanism that imparts activity to the mGRFT series of lectins, the selective binding of high mannose oligosaccharides.

The inability of the tandemers to cause viral aggregation likely stems from the conformational flexibility of the mGRFT domains. In GRFT the two domains are rigidly held against each other. When one domain of GRFT binds to an Env spike, the second domain would be oriented away at a 160° angle from that spike and is likely more available for binding the glycans on other Env spikes than glycans on the same spike. In the case of the tandemers, after binding of the first mGRFT domain to an Env spike, the flexible linkers would allow the remaining mGRFT domains to more readily sample the local environment and bind to the nearest available carbohydrate ligand. The local concentration of ligands available for subsequent mGRFT domains is potentially higher on the same spike than in the overall solution. Therefore, the tandemers, owing to the flexibility of their linkers, are more likely to bind glycans on the same spike, whereas GRFT, due to its conformational rigidity, would favor predominantly inter-virion cross-linking.

These observations have implications for understanding the mechanism whereby the GRFT tandemers neutralize HIV. The antiviral activity of GRFT, mGRFT, and the tandemers stems from their selective binding to high mannose oligosaccharides on Env spikes. Natural mutations that removed glycosylation at positions Asn234 and Asn295 have been reported to impart resistance to GRFT (Alexandre et al., *Virology*, 402(1): 187-96 (2010)). In addition, deglycosylation of gp120 at Asn295 or Asn448 also resulted in resistance to GRFT (Huang et al., *J. Gen. Virol.*, 92(10): 2367-2373 (2011)).

Mapping of Asn234, Asn295, and Asn448 glycans on trimeric spike structures suggests that glycans decorating these asparagines are located on the lateral edges of HIV spikes. The arrangement of the griffithsin monomers in the tandemers is such that they are able to bind carbohydrate moieties on the same virion, but not in a way that bridges separate virions, as demonstrated by tomographic and light scattering experiments. Given the molecular dimensions of the tandemers (<100 Å across), and the fact that neighboring spikes on the virus are spaced apart by significantly greater and variable distances (each trimeric Env itself is ~150 Å across), it follows that the multiple sites on the tandemers are occupied by carbohydrates that are displayed within the same Env trimer, with a high likelihood of crosslinking across protomers within the trimer.

Cryo-electron microscopic studies have shown that CD4-induced opening of the trimeric Env spike is necessary for exposure of gp41 that initiates the first step in the fusion of viral and target cell membranes (Liu et al., *Nature*, 455: 109-113 (2008); Tran et al., *PLoS Pathogens*, 8: e1002797 (2012); and Bartesaghi et al., *Nat. Struct. Mol. Biol.*, 20: 1352-1357 (2013)). The crosslinking of gp120 protomers may essentially block the opening of the trimeric spike and prevent exposure of gp41 and its fusogenic components required for viral entry, thus providing a likely mechanism for the potent function of GRFT and tandemers as antiviral agents.

Example 4

This example demonstrates the thermal stabilities of the GRFT tandemers.

The maintenance of the mGRFT form of individual lectin domains in the GRFT tandemers was confirmed by differential scanning calorimetry. The extrapolated midpoint of the transition (Tm) of the GRFT molecules was measured and tabulated (Table 3).

TABLE 3

Results of DSC Analysis of GRFT tandemers.

| | Tm (° C.) |
|---|---|
| GRFT* | 78.8 ± 0.0 |
| mGRFT (1GS-S)* | 63.5 ± 0.1 |
| 2mG | 61.7 ± 0.1 |
| 2mG3 | 61.3 ± 0.1 |
| 3mG | 58.5 ± 0.9 |

*Moulaei et al., Structure, 18: 1104-1015 (2010)

The GRFT tandemers all melted at temperatures below that of the native, dimeric GRFT (GRFT; Table 3) and at Tm values comparable to that mGRFT (Moulaei et al., Structure,* 18(9): 1104-15 (2010)). It was hypothesized from knowledge of the compact structure of GRFT that the tandemers would be less spatially restricted, primarily due to their flexible linker regions that were engineered within their constructs. The lower melting temperatures, however, indicated that, at least, the tandemers did not form higher-order structures that could have potentially obviated the interpretation of their structural stabilities.

Example 5

This example demonstrates that the results of isothermal titration calorimetry.

To further understand the differences in the anti-viral activity of the GRFT tandemers, isothermal titration calorimetry (ITC) was used to characterize the full thermodynamics of binding of the tandemers with the HIV envelope glycoprotein gp120, the major receptor on the virus known to bind GRFT (Mori et al., *J. Biol. Chem.,* 280(10): 9345-53 (2005)).

The gp120 binding of 2mG, 2mG3, and 3mG were fully characterized and the thermodynamic parameters of the interactions are detailed in Table 4.

TABLE 4

| Select GRFT Tandemer Properties. | | | | |
|---|---|---|---|---|
| | Affinity (μM) | ΔH (kcal/mol) | ΔG (kcal/mol) | TΔS (kcal/mol) |
| GRFT | 0.008 ± 0.004 | −30.4 ± 0.3 | −11.2 ± 0.3 | −19.2 ± 0.3 |
| mGRFT | 0.112 ± 0.050 | −35.5 ± 0.6 | −9.47 ± 0.7 | −26.0 ± 0.7 |
| 2mG | 0.005 ± 0.002 | −69.6 ± 0.5 | −11.6 ± 0.6 | −59.9 ± 0.5 |
| 2mG3 | 0.003 ± 0.001 | −47.2 ± 0.6 | −11.8 ± 0.2 | −35.4 ± 0.6 |
| 3mG | 0.003 ± 0.001 | −74.4 ± 0.4 | −11.8 ± 0.2 | −62.7 ± 0.4 |

It is clear that all binding between the tandemers and gp120 is exothermic in nature. The exothermic heats of interaction (negative ΔH values; Table 4) observed in these experiments are primarily due to polar/electrostatic interactions between GRFT and the high-mannose oligosaccharides of gp120. As observed previously for the binding between GRFT and high-mannose oligosacharides, an enthalpy-entropy compensation was apparent, indicating that the favorable binding contacts between GRFT and gp120 (negative ΔH values) had overcome not only the unfavorable conformational penalties of the bound partners but also the unfavorable entropy of water (negative TΔS values; Table 4) at the interface and around the bound complex resulting in favored binding with gp120 (negative ΔG values, Table 4).

Within experimental error for the Kd values (Table 4), the tandemers bound gp120 as well as (if not slightly better than) dimeric GRFT, particularly in the case of the 2mG3 and 3mG constructs where a 3 nM Kd was measured. However, when the tight gp120-binding affinities were parsed into their respective enthalpic and entropic quantities, the various GRFT variants could be accurately compared.

Compared to dimeric GRFT, the tandemers all appear to mediate an increased number of binding contacts with gp120 (Table 4), suggesting that the flexible tethering in these tandemer structures had allowed their monomer subunits to sample more completely their respective gp120-binding capacity. Conversely, steric hindrance and/or inflexibility in GRFT may have hampered its monomer subdomains from making full contact with gp120.

The enthalpy of binding is not the sole determinant of an optimal binding interaction. Although the 2mG and 3mG binding events were the most exothermic by nature, it was the 2mG3 construct that produced the best overall binding profile among the tandemers, showing very little entropic cost (TΔS=−35 kcal/mol) to binding. The enthalpy/entropy compensation (ΔH/ΔS) ratio for 2mG3 was the 1.33 compared to 1.16 and 1.19 for 2mG and 3mG, respectively (Table 4). As with any tethered constructs, the crosslinking and "cage-like" interactions with gp120 would be entropically disfavored primarily due to water entrapment (decreased entropy of the water) within the crosslinked complex. However, if the longer tethering in 2mG3 allowed for increased flexibility of the gp120-bound complex, then a flexible cage where water entrapment would be less due to dynamic exchange with the environment, decreasing the entropic penalty of binding, could be envisioned.

One additional observation from the ITC experiments was that, unlike native GRFT, the binding of the 2mG3 GRFT tandemer to gp120 did not result in aggregation. Both 2mG and 3mG tandemers caused aggregation when co-incubated with gp120 but not to the extent that GRFT caused. This might indicate that the increased flexibility between 2mG3 binding domains improved the likelihood that a single 2mG3 tandemer bound exclusively to a single gp120 molecule.

Example 6

This example provides the results of electron microscopy analysis.

The effect of griffithsin on suspensions of purified HIV-1 BaL virions was evaluated using cryo-electron microscopy. Control experiments were first done in which purified virions were imaged in the absence of any griffithsin constructs. These results showed a uniform distribution of HIV-1 virions in the imaging field, with virions having approximately 100 nm diameter and spherical shape.

When virions were imaged at high magnification with cryo-electron tomography, individual Envelope glycoprotein spikes were visible. The spikes were of the expected height of ~120 Å as measured from the membrane, with a structural profile consistent with previous molecular structure studies (Liu et al., *Nature,* 455(7209): 109-113 (2008); White et al., *J. Virol.,* 85(23): 12114-12123 (2011); Harris et al., *Proc. Natl. Acad. Sci. USA,* 108(28): 11440-11445 (2011); Tran et al., *PLoS Pathog.* 8(7): e1002797 (2012); Meyerson et al., *Proc. Natl. Acad. Sci. USA,* 110(2): 513-518 (2013)).

Next, experiments were done in which viruses were incubated with the engineered monomeric griffithsin (mGRFT) prior to imaging. The overall spatial distribution and shape of the viruses in the presence of mGRFT appeared similar to that of the negative control. However, when examined at higher magnification differences in spike size and structural profile were evident. Spikes exposed to mGRFT displayed an enlarged mass that was irregular in both the degree of enlargement and shape. Large patches of spikes were also observed, though it was not determined whether these patches represent the initial arrangement of spikes in the membrane, or result from cross-linking of spikes by mGRFT.

The effect of native dimeric GRFT on HIV-1 differed dramatically from that of mGRFT. Virions treated with dimeric GRFT formed large aggregates having lateral dimensions on the micrometer scale. Individual virions can be identified at the periphery of the aggregates, and though they seem to maintain their membrane integrity, their shapes are highly distorted. At higher magnification, tomography reveals dense masses of protein at the interfaces between virions. These masses consistently co-localize with distortions in virion membranes and the membrane distortions experienced by a virion follow the contour of opposing virions' membranes.

The investigation was extended to four engineered tandemer repeats of two, three and four griffithsin monomers spaced by multi-peptide linkers. The four constructs, 2mG, 2mrG3, 3mG, and 4mG displayed mutually similar effects on HIV-1 virions and Envelope. Following treatment with one of the four tandemers, virion suspensions were imaged under vitreous conditions. Projection and tomographic imaging showed that in all four experiments, virions remained monodisperse following lectin treatment. At higher magnification the tandemers were observed to decorate Envelope glycoproteins. Notably, this effect more closely resembled that of mGRFT rather than native dGRFT.

Example 7

This example demonstrates the anti-HIV activity of griffithsin tandemers.

The 2mG, 2mG3, 3mG, and 4mG tandemers, as well as wild-type dimeric GRFT, were evaluated for anti-viral activity against several clades of HIV-1, including subtypes A (Q23.17 and Q168.a2), B (PVO.4, QH0692.42, JR-FL, and CAAN5342.A2), and C (Du156.12, Du179.14, COT6.15, DU151.2, and CAP206.8). The $IC_{50}$ values of the tandemers for each clade are indicated in Table 5.

Additionally, anti-viral activity of the tandemers against viruses that are resistant to wild-type dimeric GRFT was determined. Table 6 contains the $IC_{50}$ values of the tandemers and GRFT for matched wild-type (WT) and GRFT-resistant (R) viruses. The fold reduction in activity between the WT and R viruses is shown in parentheses. The reduction of activity in the 3mG and 4mG tandemers is much less than that observed with wild-type dimeric GRFT (see Table 6).

TABLE 5

HIV-1 sensitivity to tandemers.

| Envelope | 2mG | 2mG3 | 3mG | 4mG | GRFT |
|---|---|---|---|---|---|
| | | | $IC_{50}$ (nM) | | |
| | | | Subtype B | | |
| PVO.4 | 0.301 ± 0.0818 | 0.558 ± 0.105 | 0.270 ± 0.0344 | 0.185 ± 0.0151 | 0.0370 ± 0.0173 |
| QH0692.42 | 0.202 ± 0.0842 | 0.513 ± 0.0882 | 0.223 ± 0.0151 | 0.170 ± 0.0119 | 0.0473 ± 0.0152 |
| JR-FL | 2.09 ± 1.04 | 5.77 ± 2.16 | 0.325 ± 0.0702 | 0.287 ± 0.0476 | 0.922 ± 0.354 |
| CAAN5342.A2 | 5.27 ± 3.28 | 16.9 ± 1.41 | 0.326 ± 0.0834 | 0.232 ± 0.0167 | 7.34 ± 0.927 |
| Median | 1.20 | 3.16 | 0.298 | 0.208 | 0.485 |
| | | | Subtype C | | |
| Du156.12 | 0.0182 ± 0.00133 | 0.0616 ± 0.00335 | 0.0794 ± 0.0252 | 0.0887 ± 0.0185 | 0.0324 ± 0.00205 |
| Du179.14 | 0.158 ± 0.0962 | 0.144 ± 0.0438 | 0.124 ± 0.0262 | 0.0934 ± 0.0291 | 0.606 ± 0.139 |
| COT6.15 | 1.46 ± 0.452 | 2.52 ± 1.01 | 0.412 ± 0.0588 | 0.273 ± 0.0396 | 0.734 ± 0.326 |
| DU151.2 | 0.694 ± 0.144 | 1.70 ± 0.0306 | 0.308 ± 0.0169 | 0.300 ± 0.0285 | 1.49 ± 0.225 |
| CAP206.8 | 0.178 ± 0.0750 | 0.696 ± 0.0141 | 0.181 ± 0.0546 | 0.164 ± 0.0586 | 2.14 ± 1.26 |
| Median | 0.178 | 0.696 | 0.181 | 0.164 | 0.734 |
| | | | Subtype A | | |
| Q23.17 | 7.26 ± 0.225 | 7.16 ± 0.512 | 0.462 ± 0.101 | 0.276 ± 0.0710 | 1.19 ± 0.535 |
| Q168.a2 | 1.55 ± 0.723 | 5.28 ± 1.48 | 0.331 ± 0.0398 | 0.273 ± 0.0167 | 3.80 ± 1.03 |
| Median | 4.41 | 6.22 | 0.396 | 0.274 | 2.5 |

TABLE 6

Sensitivity of matched wild-type (WT) and GRFT-resistant (R) viruses to tandemers.

| Envelope | 2MG | 2MG3 | 3MG | 4MG | GRFT |
|---|---|---|---|---|---|
| | | | $IC_{50}$ (nM) | | |
| Du179.14 (WT) | 0.158 ± 0.0962 | 0.144 ± 0.0438 | 0.124 ± 0.0262 | 0.0934 ± 0.0291 | 0.606 ± 0.139 |
| Du179 GRFT c17 (R) | 35.99 ± 0.438 (228↓) | 34.37 ± 0.629 (239↓) | 3.86 ± 0.891 (31↓) | 2.08 ± 0.629 (22↓) | >(82↓) |
| Du156.12 (WT) | 0.0182 ± 0.00133 | 0.0616 ± 0.00335 | 0.0794 ± 0.0252 | 0.0887 ± 0.0185 | 0.0324 ± 0.00205 |
| Du156R18 (R) | 27.1 ± 11.6 (1489↓) | 26.0 ± 15.7 (422↓) | 1.11 ± 0.310 (14↓) | 0.688 ± 0.201 (8↓) | 9.14 ± 5.34 (282↓) |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A construct containing two or more monomeric griffithsin molecules joined by a linker, wherein the linker is $(Gly\text{-}Thr\text{-}Gly)_n$, wherein n is 1-5, and wherein at least one monomeric griffithsin molecule comprises an insertion of two or more residues between Ser16 and Gly17.

2. The construct of claim 1 containing three monomeric griffithsin molecules joined by the linker.

3. The construct of claim 1 containing four monomeric griffithsin molecules joined by the linker.

4. The construct of claim 1, wherein the two or more residues comprise a serine.

5. The construct of claim 4, wherein the two or more residues are $(Gly\text{-}Ser)_n$, wherein n=1.

6. The construct of claim 1, wherein the two or more residues are $(Gly\text{-}Ser)_n$, wherein n=2.

7. The construct of claim 1, wherein the monomeric griffithsin is encoded by the nucleic acid sequence of SEQ ID NO: 6.

8. The construct of claim 1, wherein the construct comprises SEQ ID NO: 9, 11, 13, or 15.

9. The construct of claim 1, wherein the construct is encoded by the nucleic acid sequence of SEQ ID NO: 8, 10, 12, or 14.

10. A conjugate comprising the construct of claim 1 and at least one effector component.

11. The conjugate of claim 10, wherein the at least one effector component, which can be same or different, is selected from the group consisting of polyethylene glycol, albumin, dextran, a toxin, an immunological reagent, a virus, a viral envelope glycoprotein, an antiviral agent, and a solid support matrix.

12. A composition comprising (i) the construct of claim 1, a conjugate comprising the construct, a nucleic acid molecule encoding the construct, a recombinant vector comprising the nucleic acid molecule, or a cell comprising the nucleic acid molecule or the recombinant vector, and (ii) a carrier.

13. The construct of claim 1, wherein each monomeric griffithsin molecule comprises an insertion of two or more residues between Ser16 and Gly17.

14. A method of prophylactically or therapeutically inhibiting a viral infection in a cell or host comprising administering to the cell or host the construct of claim 1 or a composition thereof comprising the construct, such that the viral infection is inhibited.

15. The method of claim 14, wherein the viral infection is an HIV infection.

16. A method of inhibiting a virus in a biological sample or in/on an inanimate object comprising contacting the biological sample or the inanimate object with a viral-inhibiting amount of the construct of claim 1, or a composition comprising the construct, which method further comprises the prior, simultaneous, or subsequent contacting of the biological sample or inanimate object with an antiviral agent or another agent that is efficacious in inhibiting the virus, whereupon the virus is inhibited.

17. The method of claim 14, wherein the construct comprises SEQ ID NO: 9, 11, 13, or 15.

18. The method of claim 14, wherein the construct comprises SEQ ID NO: 9, 11, 13, or 15.

* * * * *

SEQUENCE LISTING

```
<160> NUMBER OF SEQ ID NOS: 15

<210> SEQ ID NO 1
<211> LENGTH: 30
<212> TYPE: DNA
<213> ORGANISM: Artificial Sequence
<220> FEATURE:
<223> OTHER INFORMATION: Synthetic

<400> SEQUENCE: 1
ggtaccgcgg gctagcatat gtcgaccggt                                          30

<210> SEQ ID NO 2
<211> LENGTH: 29
<212> TYPE: DNA
<213> ORGANISM: Artificial Sequence
<220> FEATURE:
<223> OTHER INFORMATION: Synthetic

<400> SEQUENCE: 2
ggggtaccgg cagctcgacc catcgcaag                                           29

<210> SEQ ID NO 3
<211> LENGTH: 41
<212> TYPE: DNA
<213> ORGANISM: Artificial Sequence
<220> FEATURE:
<223> OTHER INFORMATION: Synthetic

<400> SEQUENCE: 3
ggaccggtgc cgtactgttc atagtagatg tccaggctat c                             41

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4
```

```
Gly Thr Gly Gly Thr Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Gly Thr Gly Gly Thr Gly Gly Thr Gly
1               5

<210> SEQ ID NO 6
<211> LENGTH: 123
<212> TYPE: PRT
<213> ORGANISM: Artificial Sequence
<220> FEATURE:
<223> OTHER INFORMATION: Synthetic

<400> SEQUENCE: 6

Ser Ser Thr His Arg Lys Phe Gly Gly Ser Gly Gly Ser Pro Phe Ser
1               5                   10                  15

Gly Ser Gly Leu Ser Ser Ile Ala Val Arg Ser Gly Ser Tyr Leu Asp
            20                  25                  30

Ala Ile Ile Ile Asp Gly Val His His Gly Ser Gly Gly Asn Leu
        35                  40                  45

Ser Pro Thr Phe Thr Phe Gly Ser Gly Glu Tyr Ile Ser Asn Met Thr
    50                  55                  60

Ile Arg Ser Gly Asp Tyr Ile Asp Asn Ile Ser Phe Glu Thr Asn Met
65                  70                  75                  80

Gly Arg Arg Phe Gly Pro Tyr Gly Gly Ser Gly Gly Ser Ala Asn Thr
                85                  90                  95

Leu Ser Asn Val Lys Val Ile Gln Ile Asn Gly Ser Ala Gly Asp Tyr
            100                 105                 110

Leu Asp Ser Leu Asp Ile Tyr Tyr Glu Gln Tyr
        115                 120

<210> SEQ ID NO 7
<211> LENGTH: 121
<212> TYPE: PRT
<213> ORGANISM: Artificial Sequence
<220> FEATURE:
<223> OTHER INFORMATION: Synthetic

<400> SEQUENCE: 7

Ser Leu Thr His Arg Lys Phe Gly Gly Ser Gly Gly Ser Pro Phe Ser
1               5                   10                  15

Gly Leu Ser Ser Ile Ala Val Arg Ser Gly Ser Tyr Leu Asp Ala Ile
            20                  25                  30

Ile Ile Asp Gly Val His His Gly Gly Ser Gly Gly Asn Leu Ser Pro
        35                  40                  45

Thr Phe Thr Phe Gly Ser Gly Glu Tyr Ile Ser Asn Met Thr Ile Arg
    50                  55                  60

Ser Gly Asp Tyr Ile Asp Asn Ile Ser Phe Glu Thr Asn Met Gly Arg
65                  70                  75                  80

Arg Phe Gly Pro Tyr Gly Gly Ser Gly Gly Ser Ala Asn Thr Leu Ser
                85                  90                  95

Asn Val Lys Val Ile Gln Ile Asn Gly Ser Ala Gly Asp Tyr Leu Asp
```

```
                    100                 105                 110
Ser Leu Asp Ile Tyr Tyr Glu Gln Tyr
        115                 120

<210> SEQ ID NO 8
<211> LENGTH: 750
<212> TYPE: DNA
<213> ORGANISM: Artificial Sequence
<220> FEATURE:
<223> OTHER INFORMATION: Synthetic

<400> SEQUENCE: 8
agctcgaccc atcgcaagtt cggtggtagt ggtggaagtc cgttctctgg tagcggtctg      60
agcagcattg cagttcgtag tggcagctat ctggatgcga tcatcattga tggtgtacat     120
cacggtggct ctggtggtaa cctgagtccg accttcacct ttggatccgg tgagtacatc     180
agcaacatga ccattcgtag tggagactac attgacaaca tcagctttga aaccaacatg     240
ggtcgtcgct ttggtccgta tggtggatct ggtggcagtg caaacaccct gagcaacgtg     300
aaagtcatcc agatcaacgg tagtgcaggt gactatctgg atagcctgga catctactat     360
gaacagtacg gtacaggttc ttcgacccat cgcaagttcg gtggtagtgg tggaagtccg     420
ttctctggta gcggtctgag cagcattgca gttcgtagtg cagctatct ggatgcgatc      480 atcattgatg gtgtacatca cggtggctct ggtggtaacc tgagtccgac cttcaccttt     540
ggatccggtg agtacatcag caacatgacc attcgtagtg gagactacat tgacaacatc     600
agctttgaaa ccaacatggg tcgtcgcttt ggtccgtatg gtggatctgg tggcagtgca     660
aacaccctga gcaacgtgaa agtcatccag atcaacggta gtgcaggtga ctatctggat     720
agcctggaca tctactatga acagtactaa                                      750

<210> SEQ ID NO 9
<211> LENGTH: 249
<212> TYPE: PRT
<213> ORGANISM: Artificial Sequence
<220> FEATURE:
<223> OTHER INFORMATION: Synthetic

<400> SEQUENCE: 9

Ser Ser Thr His Arg Lys Phe Gly Gly Ser Gly Gly Ser Pro Phe Ser
1               5                   10                  15

Gly Ser Gly Leu Ser Ser Ile Ala Val Arg Ser Gly Ser Tyr Leu Asp
            20                  25                  30

Ala Ile Ile Ile Asp Gly Val His His Gly Ser Gly Gly Asn Leu
        35                  40                  45

Ser Pro Thr Phe Thr Phe Gly Ser Gly Glu Tyr Ile Ser Asn Met Thr
    50                  55                  60

Ile Arg Ser Gly Asp Tyr Ile Asp Asn Ile Ser Phe Glu Thr Asn Met
65                  70                  75                  80

Gly Arg Arg Phe Gly Pro Tyr Gly Gly Ser Gly Gly Ser Ala Asn Thr
                85                  90                  95

Leu Ser Asn Val Lys Val Ile Gln Ile Asn Gly Ser Ala Gly Asp Tyr
            100                 105                 110

Leu Asp Ser Leu Asp Ile Tyr Tyr Glu Gln Tyr Gly Thr Gly Ser Ser
        115                 120                 125

Thr His Arg Lys Phe Gly Gly Ser Gly Gly Ser Pro Phe Ser Gly Ser
    130                 135                 140

Gly Leu Ser Ser Ile Ala Val Arg Ser Gly Ser Tyr Leu Asp Ala Ile
```

```
                  145                 150                 155                 160
Ile Ile Asp Gly Val His His Gly Gly Ser Gly Gly Asn Leu Ser Pro
                      165                 170                 175

Thr Phe Thr Phe Gly Ser Gly Glu Tyr Ile Ser Asn Met Thr Ile Arg
                      180                 185                 190

Ser Gly Asp Tyr Ile Asp Asn Ile Ser Phe Glu Thr Asn Met Gly Arg
                      195                 200                 205

Arg Phe Gly Pro Tyr Gly Gly Ser Gly Ser Ala Asn Thr Leu Ser
    210                 215                 220

Asn Val Lys Val Ile Gln Ile Asn Gly Ser Ala Gly Asp Tyr Leu Asp
225                 230                 235                 240

Ser Leu Asp Ile Tyr Tyr Glu Gln Tyr
                245
```

<210> SEQ ID NO 10
<211> LENGTH: 1128
<212> TYPE: DNA
<213> ORGANISM: Artificial Sequence
<220> FEATURE:
<223> OTHER INFORMATION: Synthetic

<400> SEQUENCE: 10

```
agctcgaccc atcgcaagtt cggtggtagt ggtggaagtc cgttctctgg tagcggtctg      60
agcagcattg cagttcgtag tggcagctat ctggatgcga tcatcattga tggtgtacat     120
cacggtggct ctggtggtaa cctgagtccg accttcacct ttggatccgg tgagtacatc     180
agcaacatga ccattcgtag tggagactac attgacaaca tcagctttga aaccaacatg     240
ggtcgtcgct ttggtccgta tggtggatct ggtggcagtg caaacaccct gagcaacgtg     300
aaagtcatcc agatcaacgg tagtgcaggt gactatctgg atagcctgga catctactat     360
gaacagtacg gtaccggcag ctcgacccat cgcaagttcg gtggtagtgg tggaagtccg     420
ttctctggta gcggtctgag cagcattgca gttcgtagtg gcagctatct ggatgcgatc     480
atcattgatg gtgtacatca cggtggctct ggtggtaacc tgagtccgac cttcaccttt     540
ggatccggtg agtacatcag caacatgacc attcgtagtg gagactacat tgacaacatc     600
agctttgaaa ccaacatggg tcgtcgcttt ggtccgtatg gtggatctgg tggcagtgca     660
aacaccctga gcaacgtgaa agtcatccag atcaacggta gtgcaggtga ctatctggat     720
agcctggaca tctactatga acagtacggc accggttctt cgacccatcg caagttcggt     780
ggtagtggtg aagtccgttc tctggtagc ggtctgagca gcattgcagt tcgtagtggc     840
agctatctgg atgcgatcat cattgatggt gtacatcacg gtggctctgg tggtaacctg     900
agtccgacct tcacctttgg atccggtgag tacatcagca acatgaccat tcgtagtgga     960
gactacattg acaacatcag ctttgaaacc aacatgggtc gtcgctttgg tccgtatggt    1020
ggatctggtg gcagtgcaaa caccctgagc aacgtgaaag tcatccagat caacggtagt    1080
gcaggtgact atctggatag cctggacatc tactatgaac agtactaa                 1128
```

<210> SEQ ID NO 11
<211> LENGTH: 375
<212> TYPE: PRT
<213> ORGANISM: Artificial Sequence
<220> FEATURE:
<223> OTHER INFORMATION: Synthetic

<400> SEQUENCE: 11

Ser Ser Thr His Arg Lys Phe Gly Gly Ser Gly Gly Ser Pro Phe Ser

```
1               5                    10                   15
Gly Ser Gly Leu Ser Ser Ile Ala Val Arg Ser Gly Ser Tyr Leu Asp
            20                  25                  30
Ala Ile Ile Ile Asp Gly Val His His Gly Ser Gly Gly Asn Leu
            35                  40                  45
Ser Pro Thr Phe Thr Phe Gly Ser Gly Glu Tyr Ile Ser Asn Met Thr
50                      55                  60
Ile Arg Ser Gly Asp Tyr Ile Asp Asn Ile Ser Phe Glu Thr Asn Met
65                  70                  75                  80
Gly Arg Arg Phe Gly Pro Tyr Gly Ser Gly Gly Ser Ala Asn Thr
                85                  90                  95
Leu Ser Asn Val Lys Val Ile Gln Ile Asn Gly Ser Ala Gly Asp Tyr
                100                 105                 110
Leu Asp Ser Leu Asp Ile Tyr Tyr Glu Gln Tyr Gly Thr Gly Ser Ser
                115                 120                 125
Thr His Arg Lys Phe Gly Gly Ser Gly Gly Ser Pro Phe Ser Gly Ser
                130                 135                 140
Gly Leu Ser Ser Ile Ala Val Arg Ser Gly Ser Tyr Leu Asp Ala Ile
145                 150                 155                 160
Ile Ile Asp Gly Val His His Gly Gly Ser Gly Asn Leu Ser Pro
                165                 170                 175
Thr Phe Thr Phe Gly Ser Gly Glu Tyr Ile Ser Asn Met Thr Ile Arg
                180                 185                 190
Ser Gly Asp Tyr Ile Asp Asn Ile Ser Phe Glu Thr Asn Met Gly Arg
                195                 200                 205
Arg Phe Gly Pro Tyr Gly Gly Ser Gly Gly Ser Ala Asn Thr Leu Ser
210                 215                 220
Asn Val Lys Val Ile Gln Ile Asn Gly Ser Ala Gly Asp Tyr Leu Asp
225                 230                 235                 240
Ser Leu Asp Ile Tyr Tyr Glu Gln Tyr Gly Thr Gly Ser Ser Thr His
                245                 250                 255
Arg Lys Phe Gly Gly Ser Gly Gly Ser Pro Phe Ser Gly Ser Gly Leu
                260                 265                 270
Ser Ser Ile Ala Val Arg Ser Gly Ser Tyr Leu Asp Ala Ile Ile Ile
                275                 280                 285
Asp Gly Val His His Gly Gly Ser Gly Gly Asn Leu Ser Pro Thr Phe
                290                 295                 300
Thr Phe Gly Ser Gly Glu Tyr Ile Ser Asn Met Thr Ile Arg Ser Gly
305                 310                 315                 320
Asp Tyr Ile Asp Asn Ile Ser Phe Glu Thr Asn Met Gly Arg Arg Phe
                325                 330                 335
Gly Pro Tyr Gly Gly Ser Gly Gly Ser Ala Asn Thr Leu Ser Asn Val
                340                 345                 350
Lys Val Ile Gln Ile Asn Gly Ser Ala Gly Asp Tyr Leu Asp Ser Leu
                355                 360                 365
Asp Ile Tyr Tyr Glu Gln Tyr
                370                 375

<210> SEQ ID NO 12
<211> LENGTH: 1506
<212> TYPE: DNA
<213> ORGANISM: Artificial Sequence
<220> FEATURE:
<223> OTHER INFORMATION: Synthetic
```

-continued

<400> SEQUENCE: 12

```
agctcgaccc atcgcaagtt cggtggtagt ggtggaagtc cgttctctgg tagcggtctg      60
agcagcattg cagttcgtag tggcagctat ctggatgcga tcatcattga tggtgtacat     120
cacggtggct ctggtggtaa cctgagtccg accttcacct ttggatccgg tgagtacatc     180
agcaacatga ccattcgtag tggagactac attgacaaca tcagctttga aaccaacatg     240
ggtcgtcgct ttggtccgta tggtggatct ggtggcagtg caaacaccct gagcaacgtg     300
aaagtcatcc agatcaacgg tagtgcaggt gactatctgg atagcctgga catctactat     360
gaacagtacg gtaccggcag ctcgacccat cgcaagttcg gtggtagtgg tggaagtccg     420
ttctctggta gcggtctgag cagcattgca gttcgtagtg gcagctatct ggatgcgatc     480
atcattgatg gtgtacatca cggtggctct ggtggtaacc tgagtccgac cttcaccttt     540
ggatccggtg agtacatcag caacatgacc attcgtagtg gagactacat tgacaacatc     600
agctttgaaa ccaacatggg tcgtcgcttt ggtccgtatg gtggatctgg tggcagtgca     660
aacaccctga gcaacgtgaa agtcatccag atcaacggta gtgcaggtga ctatctggat     720
agcctggaca tctactatga acagtacggt acaggttctt cgacccatcg caagttcggt     780
ggtagtggtg aagtccgttc tctggtagcg gtctgagcag cattgcagtc gtagtggc      840
agctatctgg atgcgatcat cattgatggt gtacatcacg gtggctctgg tggtaacctg     900
agtccgacct tcacctttgg atccggtgag tacatcagca acatgaccat cgtagtgga      960
gactacattg acaacatcag ctttgaaacc aacatgggtc gtcgctttgg tccgtatggt    1020
ggatctggtg gcagtgcaaa caccctgagc aacgtgaaag tcatccagat caacggtagt    1080
gcaggtgact atctggatag cctggacatc tactatgaac agtacggcac cggttcttcg    1140
acccatcgca gttcggtgg tagtggtgga agtccgttct ctggtagcgg tctgagcagc    1200
attgcagttc gtagtggcag ctatctggat gcgatcatca ttgatggtgt acatcacggt    1260
ggctctggtg gtaacctgag tccgaccttc acctttggat ccggtgagta catcagcaac    1320
atgaccattc gtagtggaga ctacattgac aacatcagct ttgaaaccaa catgggtcgt    1380
cgctttggtc cgtatggtgg atctggtggc agtgcaaaca ccctgagcaa cgtgaaagtc    1440
atccagatca acggtagtgc aggtgactat ctggatagcc tggacatcta ctatgaacag    1500
tactaa                                                                1506
```

<210> SEQ ID NO 13
<211> LENGTH: 501
<212> TYPE: PRT
<213> ORGANISM: Artificial Sequence
<220> FEATURE:
<223> OTHER INFORMATION: Synthetic

<400> SEQUENCE: 13

```
Ser Ser Thr His Arg Lys Phe Gly Gly Ser Gly Gly Ser Pro Phe Ser
1               5                  10                  15

Gly Ser Gly Leu Ser Ser Ile Ala Val Arg Ser Gly Ser Tyr Leu Asp
            20                  25                  30

Ala Ile Ile Ile Asp Gly Val His His Gly Gly Ser Gly Gly Asn Leu
        35                  40                  45

Ser Pro Thr Phe Thr Phe Gly Ser Gly Glu Tyr Ile Ser Asn Met Thr
    50                  55                  60

Ile Arg Ser Gly Asp Tyr Ile Asp Asn Ile Ser Phe Glu Thr Asn Met
65                  70                  75                  80
```

-continued

```
Gly Arg Arg Phe Gly Pro Tyr Gly Gly Ser Gly Gly Ser Ala Asn Thr
                85                  90                  95

Leu Ser Asn Val Lys Val Ile Gln Ile Asn Gly Ser Ala Gly Asp Tyr
            100                 105                 110

Leu Asp Ser Leu Asp Ile Tyr Tyr Glu Gln Tyr Gly Thr Gly Ser Ser
        115                 120                 125

Thr His Arg Lys Phe Gly Gly Ser Gly Gly Ser Pro Phe Ser Gly Ser
    130                 135                 140

Gly Leu Ser Ser Ile Ala Val Arg Ser Gly Ser Tyr Leu Asp Ala Ile
145                 150                 155                 160

Ile Ile Asp Gly Val His His Gly Gly Ser Gly Gly Asn Leu Ser Pro
                165                 170                 175

Thr Phe Thr Phe Gly Ser Gly Glu Tyr Ile Ser Asn Met Thr Ile Arg
            180                 185                 190

Ser Gly Asp Tyr Ile Asp Asn Ile Ser Phe Glu Thr Asn Met Gly Arg
        195                 200                 205

Arg Phe Gly Pro Tyr Gly Gly Ser Gly Gly Ser Ala Asn Thr Leu Ser
    210                 215                 220

Asn Val Lys Val Ile Gln Ile Asn Gly Ser Ala Gly Asp Tyr Leu Asp
225                 230                 235                 240

Ser Leu Asp Ile Tyr Tyr Glu Gln Tyr Gly Thr Gly Ser Ser Thr His
                245                 250                 255

Arg Lys Phe Gly Gly Ser Gly Gly Ser Pro Phe Ser Gly Ser Gly Leu
            260                 265                 270

Ser Ser Ile Ala Val Arg Ser Gly Ser Tyr Leu Asp Ala Ile Ile Ile
        275                 280                 285

Asp Gly Val His His Gly Gly Ser Gly Gly Asn Leu Ser Pro Thr Phe
    290                 295                 300

Thr Phe Gly Ser Gly Glu Tyr Ile Ser Asn Met Thr Ile Arg Ser Gly
305                 310                 315                 320

Asp Tyr Ile Asp Asn Ile Ser Phe Glu Thr Asn Met Gly Arg Arg Phe
                325                 330                 335

Gly Pro Tyr Gly Gly Ser Gly Gly Ser Ala Asn Thr Leu Ser Asn Val
            340                 345                 350

Lys Val Ile Gln Ile Asn Gly Ser Ala Gly Asp Tyr Leu Asp Ser Leu
        355                 360                 365

Asp Ile Tyr Tyr Glu Gln Tyr Gly Thr Gly Ser Ser Thr His Arg Lys
    370                 375                 380

Phe Gly Gly Ser Gly Gly Ser Pro Phe Ser Gly Ser Gly Leu Ser Ser
385                 390                 395                 400

Ile Ala Val Arg Ser Gly Ser Tyr Leu Asp Ala Ile Ile Ile Asp Gly
                405                 410                 415

Val His His Gly Gly Ser Gly Gly Asn Leu Ser Pro Thr Phe Thr Phe
            420                 425                 430

Gly Ser Gly Glu Tyr Ile Ser Asn Met Thr Ile Arg Ser Gly Asp Tyr
        435                 440                 445

Ile Asp Asn Ile Ser Phe Glu Thr Asn Met Gly Arg Arg Phe Gly Pro
    450                 455                 460

Tyr Gly Gly Ser Gly Gly Ser Ala Asn Thr Leu Ser Asn Val Lys Val
465                 470                 475                 480

Ile Gln Ile Asn Gly Ser Ala Gly Asp Tyr Leu Asp Ser Leu Asp Ile
                485                 490                 495

Tyr Tyr Glu Gln Tyr
```

<210> SEQ ID NO 14
<211> LENGTH: 768
<212> TYPE: DNA
<213> ORGANISM: Artificial Sequence
<220> FEATURE:
<223> OTHER INFORMATION: Synthetic

<400> SEQUENCE: 14

```
agctcgaccc atcgcaagtt cggtggtagt ggtggaagtc cgttctctgg tagcggtctg      60
agcagcattg cagttcgtag tggcagctat ctggatgcga tcatcattga tggtgtacat     120
cacggtggct ctggtggtaa cctgagtccg accttcacct ttggatccgg tgagtacatc     180
agcaacatga ccattcgtag tggagactac attgacaaca tcagctttga aaccaacatg     240
ggtcgtcgct ttggtccgta tggtggatct ggtggcagtg caaacaccct gagcaacgtg     300
aaagtcatcc agatcaacgg tagtgcaggt gactatctgg atagcctgga catctactat     360
gaacagtacg gtaccggcgg tacaggtggc accggttctt cgacccatcg caagttcggt     420
ggtagtggtg aagtccgttc tctggtagc ggtctgagca gcattgcagt tcgtagtggc      480
agctatctgg atgcgatcat cattgatggt gtacatcacg gtggctctgg tggtaacctg     540
agtccgacct tcacctttgg atccggtgag tacatcagca acatgaccat tcgtagtgga     600
gactacattg acaacatcag ctttgaaacc aacatgggtc gtcgctttgg tccgtatggt     660
ggatctggtg gcagtgcaaa caccctgagc aacgtgaaag tcatccagat caacggtagt     720
gcaggtgact atctggatag cctggacatc tactatgaac agtactaa                  768
```

<210> SEQ ID NO 15
<211> LENGTH: 255
<212> TYPE: PRT
<213> ORGANISM: Artificial Sequence
<220> FEATURE:
<223> OTHER INFORMATION: Synthetic

<400> SEQUENCE: 15

Ser Ser Thr His Arg Lys Phe Gly Gly Ser Gly Gly Ser Pro Phe Ser
1               5                   10                  15

Gly Ser Gly Leu Ser Ser Ile Ala Val Arg Ser Gly Ser Tyr Leu Asp
            20                  25                  30

Ala Ile Ile Ile Asp Gly Val His His Gly Gly Ser Gly Gly Asn Leu
        35                  40                  45

Ser Pro Thr Phe Thr Phe Gly Ser Gly Glu Tyr Ile Ser Asn Met Thr
    50                  55                  60

Ile Arg Ser Gly Asp Tyr Ile Asp Asn Ile Ser Phe Glu Thr Asn Met
65                  70                  75                  80

Gly Arg Arg Phe Gly Pro Tyr Gly Gly Ser Gly Gly Ser Ala Asn Thr
                85                  90                  95

Leu Ser Asn Val Lys Val Ile Gln Ile Asn Gly Ser Ala Gly Asp Tyr
            100                 105                 110

Leu Asp Ser Leu Asp Ile Tyr Tyr Glu Gln Tyr Gly Thr Gly Gly Thr
        115                 120                 125

Gly Gly Thr Gly Ser Ser Thr His Arg Lys Phe Gly Gly Ser Gly Gly
    130                 135                 140

Ser Pro Phe Ser Gly Ser Gly Leu Ser Ser Ile Ala Val Arg Ser Gly
145                 150                 155                 160

Ser Tyr Leu Asp Ala Ile Ile Ile Asp Gly Val His His Gly Gly Ser

-continued

```
              165                 170                 175

Gly Gly Asn Leu Ser Pro Thr Phe Thr Phe Gly Ser Gly Glu Tyr Ile
            180                 185                 190

Ser Asn Met Thr Ile Arg Ser Gly Asp Tyr Ile Asp Asn Ile Ser Phe
        195                 200                 205

Glu Thr Asn Met Gly Arg Arg Phe Gly Pro Tyr Gly Gly Ser Gly Gly
    210                 215                 220

Ser Ala Asn Thr Leu Ser Asn Val Lys Val Ile Gln Ile Asn Gly Ser
225                 230                 235                 240

Ala Gly Asp Tyr Leu Asp Ser Leu Asp Ile Tyr Tyr Glu Gln Tyr
              245                 250                 255
```

UNITED STATES PATENT AND TRADEMARK OFFICE
CERTIFICATE OF CORRECTION

PATENT NO. : 9,982,025 B2
APPLICATION NO. : 14/895349
DATED : May 29, 2018
INVENTOR(S) : Barry R. O'Keefe, Alexander Wlodawer and Tinoush Moulaei It is certified that error appears in the above-identified patent and that said Letters Patent is hereby corrected as shown below:

On the Title Page (*) Notice should read: Subject to any disclaimer, the term of this patent is extended or adjusted under 35 U.S.C. 154(b) by 0 days.

In the Claims

Column 44, Lines 46-47 Claim 18 should read as:
18. The method of claim 16, wherein the construct comprises SEQ ID NO: 9, 11, 13, or 15.

Signed and Sealed this
Twenty-first Day of August, 2018

Andrei Iancu
*Director of the United States Patent and Trademark Office*